United States Patent
Chiu et al.

(10) Patent No.: US 7,250,041 B2
(45) Date of Patent: Jul. 31, 2007

(54) RETROGRADE PRESSURE REGULATED INFUSION

(75) Inventors: Jessica Chiu, Belmont, CA (US); Gregory Waimong Chan, Mountain View, CA (US); Hongzhi Bai, Sunnyvale, CA (US); Nianjiong J. Bei, Poster City, CA (US); Mark J. Bly, Stanford, CA (US); Srinivasan Sridharan, Morgan Hill, CA (US); Tom Hatten, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 10/387,048

(22) Filed: Mar. 12, 2003

(65) Prior Publication Data

US 2004/0181206 A1   Sep. 16, 2004

(51) Int. Cl.
*A61M 25/00* (2006.01)
(52) U.S. Cl. .................. 604/523; 604/510; 604/96.01; 604/97.01; 604/508; 604/509
(58) Field of Classification Search ............. 604/96.01, 604/97.01, 508, 509, 103.01, 103.07, 523, 604/510
See application file for complete search history.

(56) References Cited

U.S. PATENT DOCUMENTS 4,171,698 A   10/1979   Genese (Continued)

FOREIGN PATENT DOCUMENTS

CH   671883   10/1989

(Continued)

OTHER PUBLICATIONS

Verma, Subodh, MD, et al., Fundamentals of Reperfusion Injury for the Clinical Cardiologist (Circulation, 2002 (105:2332-2336)).

(Continued)

*Primary Examiner*—Kevin C. Sirmons
*Assistant Examiner*—Phillip Gray
(74) *Attorney, Agent, or Firm*—Blakely Sokoloff Taylor & Zafman LLP

(57) ABSTRACT

A delivery catheter that includes a flexible shaft having a proximal end and a distal end, the distal end having an outer diameter less than about 13 mm; a delivery lumen having a proximal end and a distal end, the delivery lumen within the flexible shaft, the delivery lumen having at least an outlet port or at least one side hole at the distal end of the delivery lumen, the delivery lumen having a cross-sectional area at least about 5 $mm^2$; a pressure monitoring lumen having a proximal end and a distal end, the pressure monitoring lumen within the flexible shaft; a pressure port adjacent to and connected to the distal end of the pressure monitoring lumen; a balloon inflation lumen having a proximal end and a distal end, the balloon inflation lumen within the flexible shaft; a soft tip at the distal end of the flexible shaft; a balloon at the distal end of the flexible shaft, the balloon connected to the distal end of the balloon inflation lumen, the balloon includes at least one of the following materials, polyether block amide resin, polyetheramide, polyurethane, silicone, natural latex, or synthetic latex; wherein the balloon is adapted to inflate to a diameter range of about 4 to about 15 mm.

5 Claims, 20 Drawing Sheets

U.S. PATENT DOCUMENTS

| | | | |
|---|---|---|---|
| 4,313,440 A | 2/1982 | Ashley | |
| 4,424,057 A | 1/1984 | House | |
| 4,459,977 A * | 7/1984 | Pizon et al. | 600/17 |
| 4,465,476 A | 8/1984 | Gahwiler | |
| 4,516,969 A | 5/1985 | Kintner | |
| 4,581,016 A | 4/1986 | Gettig | |
| 4,642,102 A | 2/1987 | Ohmori | |
| 4,685,910 A | 8/1987 | Schweizer | |
| 4,689,041 A | 8/1987 | Corday et al. | |
| 4,693,706 A | 9/1987 | Ennis, III | |
| 4,702,737 A | 10/1987 | Pizinno | |
| 4,772,273 A | 9/1988 | Alchas | |
| 4,850,969 A | 7/1989 | Jackson | |
| 4,927,412 A | 5/1990 | Menasche | |
| 5,021,045 A | 6/1991 | Buckberg et al. | |
| 5,024,668 A | 6/1991 | Peters et al. | |
| 5,032,117 A | 7/1991 | Motta | |
| 5,033,998 A | 7/1991 | Corday et al. | |
| 5,053,008 A | 10/1991 | Bajaj | |
| 5,059,178 A | 10/1991 | Ya | |
| 5,092,841 A * | 3/1992 | Spears | 604/103.01 |
| 5,181,909 A | 1/1993 | McFarlane | |
| 5,226,427 A | 7/1993 | Buckberg et al. | |
| 5,265,622 A | 11/1993 | Barbere | |
| 5,324,266 A | 6/1994 | Ambrisco | |
| 5,328,471 A | 7/1994 | Slepian | |
| 5,374,250 A | 12/1994 | Dixon | |
| 5,385,548 A | 1/1995 | Williams et al. | |
| 5,395,331 A | 3/1995 | O'Neill et al. | |
| 5,423,744 A | 6/1995 | Gencheff et al. | |
| 5,433,735 A | 7/1995 | Zanakis et al. | |
| 5,460,611 A | 10/1995 | Alexander | |
| 5,464,395 A | 11/1995 | Faxon et al. | |
| 5,533,957 A | 7/1996 | Aldea | |
| 5,575,773 A | 11/1996 | Song et al. | |
| 5,597,377 A | 1/1997 | Aldea | |
| 5,620,418 A | 4/1997 | O'Neill et al. | |
| 5,662,607 A | 9/1997 | Booth et al. | |
| 5,662,609 A | 9/1997 | Slepian | |
| 5,674,195 A | 10/1997 | Truthan | |
| 5,674,287 A | 10/1997 | Slepian et al. | |
| 5,702,368 A | 12/1997 | Stevens et al. | |
| 5,707,358 A | 1/1998 | Wright | |
| 5,720,726 A | 2/1998 | Marcadis et al. | |
| 5,720,727 A | 2/1998 | Alexander et al. | |
| 5,749,922 A | 5/1998 | Slepian et al. | |
| 5,762,633 A | 6/1998 | Whisson | |
| 5,769,812 A | 6/1998 | Stevens et al. | |
| 5,779,685 A | 7/1998 | Thompson et al. | |
| 5,785,662 A | 7/1998 | Alexander | |
| 5,795,325 A | 8/1998 | Valley et al. | |
| 5,800,538 A | 9/1998 | Slepian et al. | |
| 5,807,326 A | 9/1998 | O'Neill et al. | |
| 5,814,016 A | 9/1998 | Valley et al. | |
| 5,814,022 A | 9/1998 | Antanavich et al. | |
| 5,814,097 A | 9/1998 | Sterman et al. | |
| 5,833,659 A | 11/1998 | Kranys | |
| 5,846,228 A | 12/1998 | Alexander | |
| 5,858,990 A | 1/1999 | Walsh | |
| 5,865,801 A * | 2/1999 | Houser | 604/103.07 |
| 5,879,336 A | 3/1999 | Brinon | |
| 5,879,499 A | 3/1999 | Corvi | |
| 5,913,842 A | 6/1999 | Boyd et al. | |
| 5,944,710 A | 8/1999 | Dev et al. | |
| 5,947,977 A | 9/1999 | Slepian et al. | |
| 5,964,735 A | 10/1999 | Alexander | |
| 5,968,013 A | 10/1999 | Smith et al. | |
| 5,989,237 A | 11/1999 | Fowles et al. | |
| 5,993,418 A | 11/1999 | Alexander | |
| 6,007,476 A | 12/1999 | Wascher et al. | |
| 6,019,750 A | 2/2000 | Fowles et al. | |
| 6,022,339 A | 2/2000 | Fowles et al. | |
| 6,024,739 A | 2/2000 | Ponzi et al. | |
| 6,063,068 A | 5/2000 | Fowles et al. | |
| 6,071,270 A | 6/2000 | Fowles et al. | |
| 6,083,215 A | 7/2000 | Milavetz | |
| 6,090,091 A | 7/2000 | Fowles et al. | |
| 6,090,092 A | 7/2000 | Fowles et al. | |
| 6,113,583 A | 9/2000 | Fowles et al. | |
| 6,123,084 A | 9/2000 | Jandak et al. | |
| 6,159,192 A | 12/2000 | Fowles et al. | |
| 6,161,731 A | 12/2000 | Sigg | |
| 6,186,972 B1 | 2/2001 | Nelson et al. | |
| 6,234,996 B1 | 5/2001 | Bagaoisan et al. | |
| 6,283,127 B1 | 9/2001 | Sterman et al. | |
| 6,287,320 B1 | 9/2001 | Slepian | |
| 6,287,430 B1 | 9/2001 | Matsumoto et al. | |
| 6,346,098 B1 | 2/2002 | Yock et al. | |
| 6,443,941 B1 | 9/2002 | Slepian et al. | |
| 6,482,171 B1 | 11/2002 | Corvi et al. | |
| 6,485,500 B1 | 11/2002 | Kokish et al. | |
| 6,500,145 B1 | 12/2002 | Bicakci | |
| 6,569,145 B1 | 5/2003 | Shmulewitz et al. | |
| 6,582,415 B1 | 6/2003 | Fowles et al. | |
| 6,610,040 B1 | 8/2003 | Fowles et al. | |
| 6,626,862 B1 | 9/2003 | Duchon et al. | |
| 6,641,562 B1 | 11/2003 | Peterson | |
| 2001/0031986 A1 | 10/2001 | Hauck | |
| 2001/0044624 A1 | 11/2001 | Seraj et al. | |
| 2002/0010492 A1 | 1/2002 | Donovan et al. | |
| 2002/0022863 A1 | 2/2002 | Hauck | |
| 2002/0026228 A1 | 2/2002 | Schauerte | |
| 2003/0187411 A1 | 10/2003 | Constantz | |

FOREIGN PATENT DOCUMENTS

| | | |
|---|---|---|
| DE | 19526784 | 1/1997 |
| EP | 0 841 073 A2 | 5/1998 |
| EP | 1 118 348 A2 | 7/2001 |
| EP | 1 208 867 A2 | 5/2002 |
| WO | WO 95/16476 | 6/1995 |
| WO | WO 96/30073 | 10/1996 |
| WO | WO 96/40346 A1 | 12/1996 |
| WO | WO-98/38930 | 9/1998 |
| WO | WO 99/04836 | 2/1999 |
| WO | WO 00/10631 | 3/2000 |
| WO | WO 01/00268 A1 | 1/2001 |
| WO | WO 01/10313 A1 | 2/2001 |
| WO | WO 01/13983 A2 | 3/2001 |
| WO | WO 02/05887 A2 | 1/2002 |

OTHER PUBLICATIONS

Novalija, E., et al., Sevoflurane Mimics Ischemic Preconditioning Effects On Coronary Flow And Nitric Oxide Release In Isolated Hearts (Anesthesiology, Sep. 1, 1999, 91(3) 701-12).

Angelos, Mark G., MD, et al., Left Ventricular Myocardial Adenosine Triphosphate Changes During Reperfusion of Ventricular Fibrillation: The Influence of Flow and Epinephrine (Critical Care Medicine, vol. 28, No. 5, May 2000).

Yost, C. Spencer, MD, Anesthetic Considerations For Minimally Invasive Cardiovascular Procedures (Anesthesiology Clinics of North America, vol. 17, No. 2, Jun. 1999).

Braunwald, Eugene, MD, et al., Heart Disease-A Textbook of Cardiovascular Medicine (6th ed., Copyright 2001).

PCT Search report dated Oct. 29, 2004 of PCT/US2004/007735, Mar. 12, 2004.

von Degenfeld, Georges, MD et al., "MSelective Pressure-Regulated Retroinfusion of Fibroblast Growth Factor-2 Into the Coronary Vein Enhances Regional Myocardial Blood Flow and Function in Pigs With Chronic Myocardial Ischemia", Journal of the American College of Cardiology, 9 pages, vol. 42, No. 6, 2003.

Boekstegers P. et al., "Myocardial Gene Transfer by Selective Pressure-Regulated Retroinfusion of Coronary Veins", Circulation, (abstract), 1 page, Jun. 6, 2000.

Lebherz, Corinna et al., "Therapeutic Angiogenesis/Arteriogenesis in the Chronic Ischemic Rabbit Hindlimb: Effect of Venous Basic Fibroblast Growth Factor Retroinfusion", Taylor & Francis, 2 pages, Jul.-Oct. 2003.

Gerber, Thomas C., MD et al., "The Coronary Venous System: An Alternate Portal to the Myocardium of Diagnostic and Therapeutic Procedures in Invasive Cardiology", Current Interventional Cardiology Reports, 19 pages, 2000.

Boekstegers, P. et al, Selective Suction and Pressure-Regulated Retroinfusion: an Effective and Safe Approach to Retrograde Protection Against Myocardial Ischemia in Patients Undergoing Normal and High Risk Percutaneou Transluminal Coronary Angioplasty, J Am Coll Cariol, 2 pages, Jun. 31, 1998.

Raake, Philip et al., "Percutaneous Approach to a Stent-Based Ventricle to Coronary Vein Bypass (venous VPASS™): Comparison to Catheter-Based Selective Pressure-Regulated Retro-Infusion of the Coronary Vein", The European Society of Cardiology, 10 pages, Feb. 25, 2005.

Gerber, Thomas C. et al., "The Coronary Venous System: An Alternate Portal to the Myocardium for Diagnostic and Therapeutic Procedures in Invasive Cardiology", Current Interventional Cardiology Reports, 11 pages, 2000.

Raake, Philip, MD et al., "Myocardial Gene Transfer by Selective Pressure-Regulated Retroinfusion of Coronary Veins", Journal of the American College of Cardiology, 6 pages, vol. 44, No. 5, 2004.

Al-Khadra, A., et al., "The Role of Electroporation in Defibrillation," Circulation Research, vol. 87, American Heart Association, Inc. (Oct. 27, 2000) pp. 797-804.

Kanno, S., et al., "Establishment of a Simple and Practical Procedure Applicable to Therapeutic Angiogensis," Circulation, vol. 99, American Heart Association, Inc. (May 25, 1999) pp. 2682-2687.

Labhasetwar, V., et al., "Iontophoresis for modulation of cardiac drug delivery in dogs," Proc. Natl. Acad. Sci. USA, Medical Sciences, vol. 92 (Mar. 1995) pp. 2612-2626.

* cited by examiner

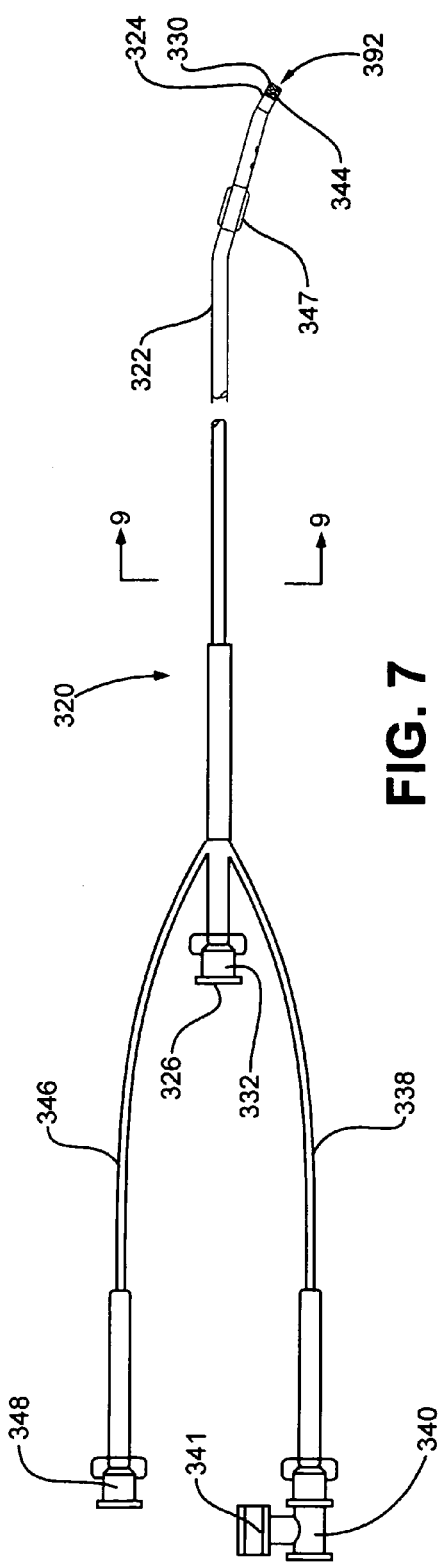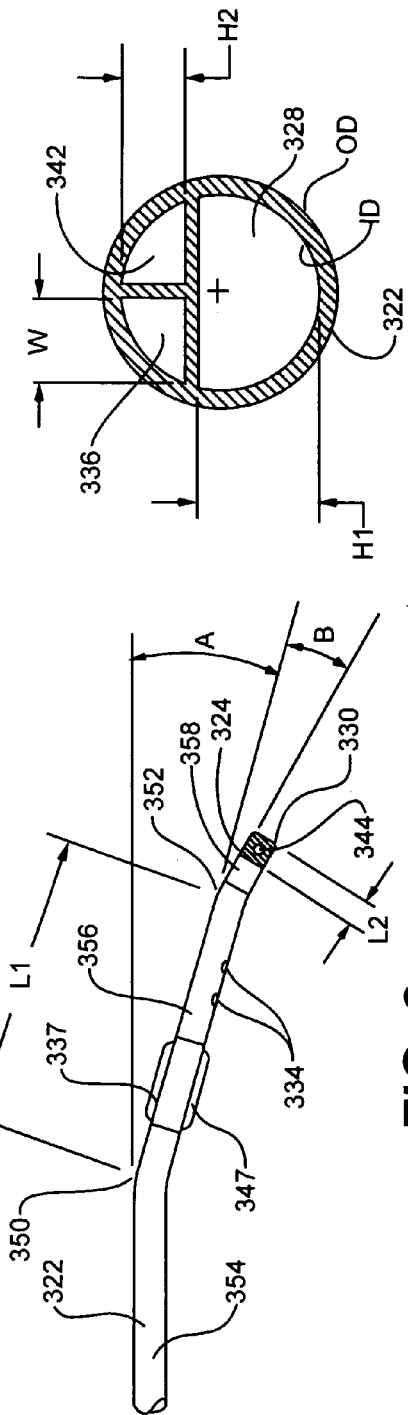

RETROGRADE PRESSURE REGULATED INFUSION

BACKGROUND

1. Field of the Invention
Cardiovascular catheters.

2. Description of Related Art

Generally, cardiovascular catheters are known in the art.
U.S. Pat. No. 4,927,412 discloses a coronary sinus catheter.
U.S. Pat. No. 5,021,045 discloses a retrograde cardioplegia catheter.
U.S. Pat. No. 5,226,427 discloses a stylet.
U.S. Pat. No. 5,385,548 discloses a catheter for retrograde perfusion of the heart.
U.S. Pat. No. 5,597,377 discloses a catheter for retroperfusion.
U.S. Pat. No. 5,620,418 discloses a coronary sinus catheter.
U.S. Pat. No. 5,662,607 discloses a catheter for supplying liquid to the coronary sinus.
U.S. Pat. No. 5,707,358 discloses a perfusion catheter for use in open heart surgery.
U.S. Pat. No. 5,720,726 discloses a catheter for retrograde perfusion of the heart.
U.S. Pat. No. 5,779,685 discloses a retrograde cardioplegia catheter.
U.S. Pat. No. 5,807,326 discloses a coronary sinus catheter assembly.
U.S. Pat. No. 5,879,499 discloses a process for forming a multi-lumen catheter.
U.S. Pat. No. 5,913,842 discloses a retrograde delivery catheter.
U.S. Pat. No. 5,916,193 discloses a venting catheter, system and method for use.
U.S. Pat. No. 5,967,988 discloses a retrograde coronary sinus perfusion catheter.
U.S. Pat. No. 6,071,271 discloses a catheter system for use in minimally invasive cardiac surgical procedures.
U.S. Pat. No. 6,241,699 discloses a catheter system and method of use.
U.S. Pat. No. 6,340,356 discloses an intraluminal catheter.
U.S. Pat. No. 6,458,323 discloses a method for selective perfusion of fluids through blood vessels.
U.S. patent application Ser. No. 09/822,678, which published as Publication No. 2001/0044624, discloses a combination method and system for intravascularly accessing and visualizing a body structure.
Copending U.S. Application having Ser. No. 10/246,249, filed on Sep. 18, 2002, discloses devices and methods to stimulate therapeutic angiogenesis. U.S. application Ser. No. 10/246,249 is herein incorporated by reference in its entirety.
Copending U.S. Application having Ser. No. 10/293,535, filed on Nov. 12, 2002, discloses a guide catheter. U.S. application Ser. No. 10/293,535 is herein incorporated by reference in its entirety.

SUMMARY

In one embodiment there is disclosed a delivery catheter that includes a flexible shaft having a proximal end and a distal end, the distal end having an outer diameter less than about 15 mm; a delivery lumen having a proximal end and a distal end, the delivery lumen within the flexible shaft, the delivery lumen having at least an outlet port or at least one side hole at the distal end of the delivery lumen, the delivery lumen having a cross-sectional area at least about 5 mm$^2$; a pressure monitoring lumen having a proximal end and a distal end, the pressure monitoring lumen within the flexible shaft; a pressure port adjacent to and connected to the distal end of the pressure monitoring lumen; a balloon inflation lumen having a proximal end and a distal end, the balloon inflation lumen within the flexible shaft; a soft tip at the distal end of the flexible shaft; a balloon at the distal end of the flexible shaft, the balloon connected to the distal end of the balloon inflation lumen, the balloon includes at least one of the following materials, polyether block amide resin, polyetheramide, polyurethane, silicone, natural latex, or synthetic latex; wherein the balloon is adapted to inflate to a diameter range of about 4 to about 15 mm.

In another embodiment, there is disclosed a catheter kit that includes a delivery catheter, a guide catheter adapted to receive the delivery catheter, a pressure increasing device adapted to be connected to the delivery catheter, a pressure sensing device adapted to be connected to connected to the delivery catheter, an inflation device adapted to be connected to the delivery catheter, and a guidewire adapted to be received within the guide catheter.

In another embodiment, there is disclosed a method of providing treatment in a vessel of a patient that includes placing a delivery catheter in the vessel of the patient, measuring the pressure in the vessel adjacent to a distal end of the catheter, inflating a balloon at the distal end of the catheter, stopping inflation of the balloon when a measured pressure waveform becomes ventricularized, forcing the liquid that includes either a drug and/or a treatment agent through the catheter to an outlet port on the catheter distal to the balloon, stopping the forcing of liquid, deflating the balloon, and removing the catheter from the vessel.

Additional features, embodiments, and benefits will be evident in view of the figures and detailed description presented herein.

BRIEF DESCRIPTION OF THE DRAWINGS

The features, aspects, and advantages of the invention will become more thoroughly apparent from the following detailed description, appended claims, and accompanying drawings in which:

FIG. 7 schematically illustrates a side elevational view of a delivery catheter;

FIG. 8 schematically illustrates a side view of the distal portion of the delivery catheter of FIG. 7;

FIG. 9 schematically illustrates a transverse cross-section of the delivery catheter of FIG. 7 taken along the line 9—9;

DETAILED DESCRIPTION

Figure 1:
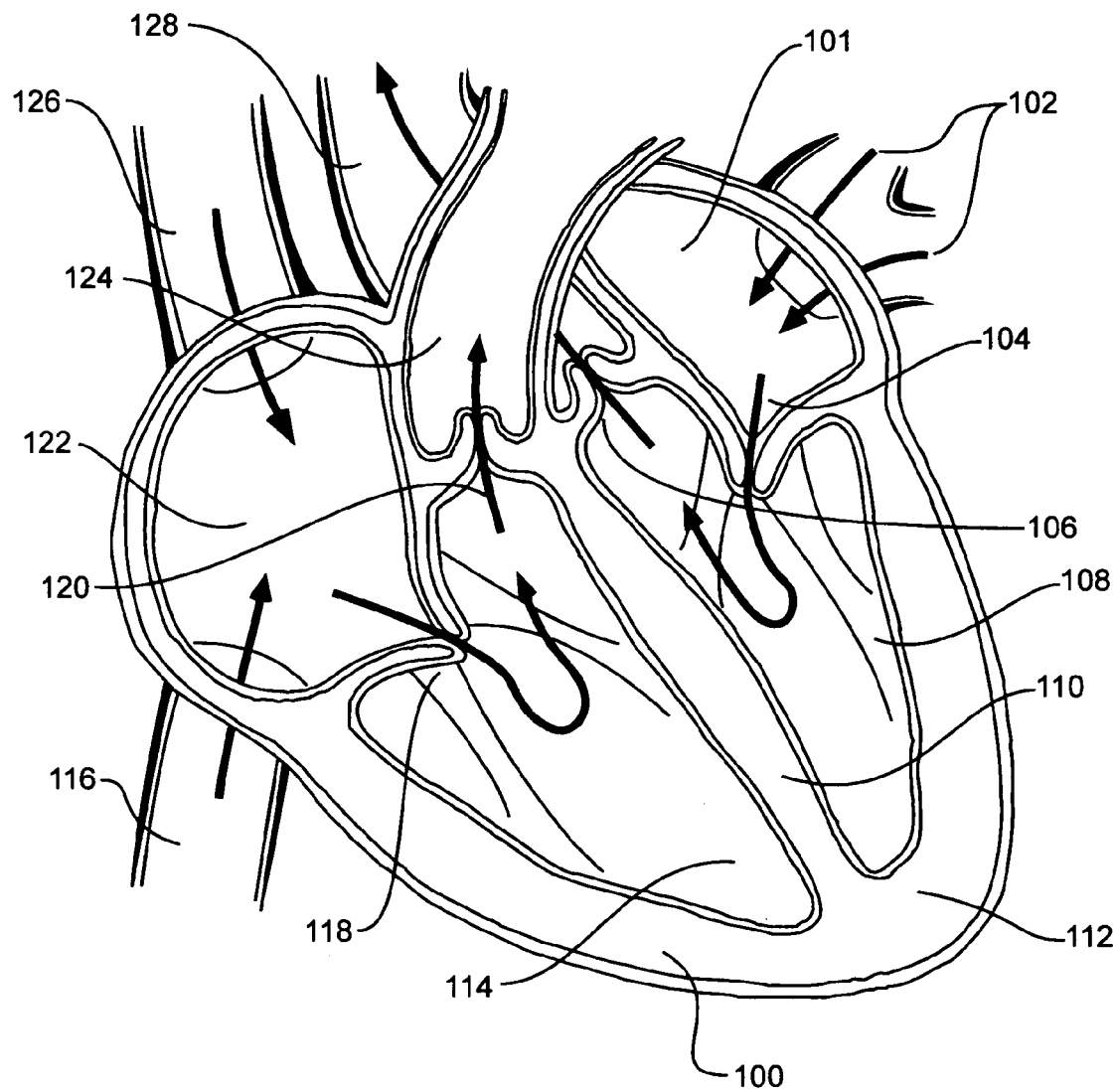
FIG. 1 schematically illustrates a cross-section of the heart showing blood flow throughout the heart.

Referring first to FIG. 1, a simplistic cross-sectional view of a heart is shown to illustrate blood flow throughout the heart.

Deoxygenated blood returning from the body comes into heart 100 from either superior vena cava 126 or inferior vena cava 116 and collects in right atrium 122. Right atrium 122 contracts to pump the blood through tricuspid valve 118 where it flows into right ventricle 114. Right ventricle 114 contracts to send the blood through pulmonary valve 120 into pulmonary artery 124 where it goes into the lungs (not shown). The oxygenated blood returning from the lungs flows through pulmonary veins 102 where it flows into left atrium 101. Left atrium 101 contracts sending the blood through bicuspid or mitral valve 104 and into left ventricle 108. When left ventricle 108 contracts, the blood is sent through aortic valve 106 and into aorta 128. Left ventricle 108 and right ventricle 114 are separated by ventricular septum 110.

Figure 2:
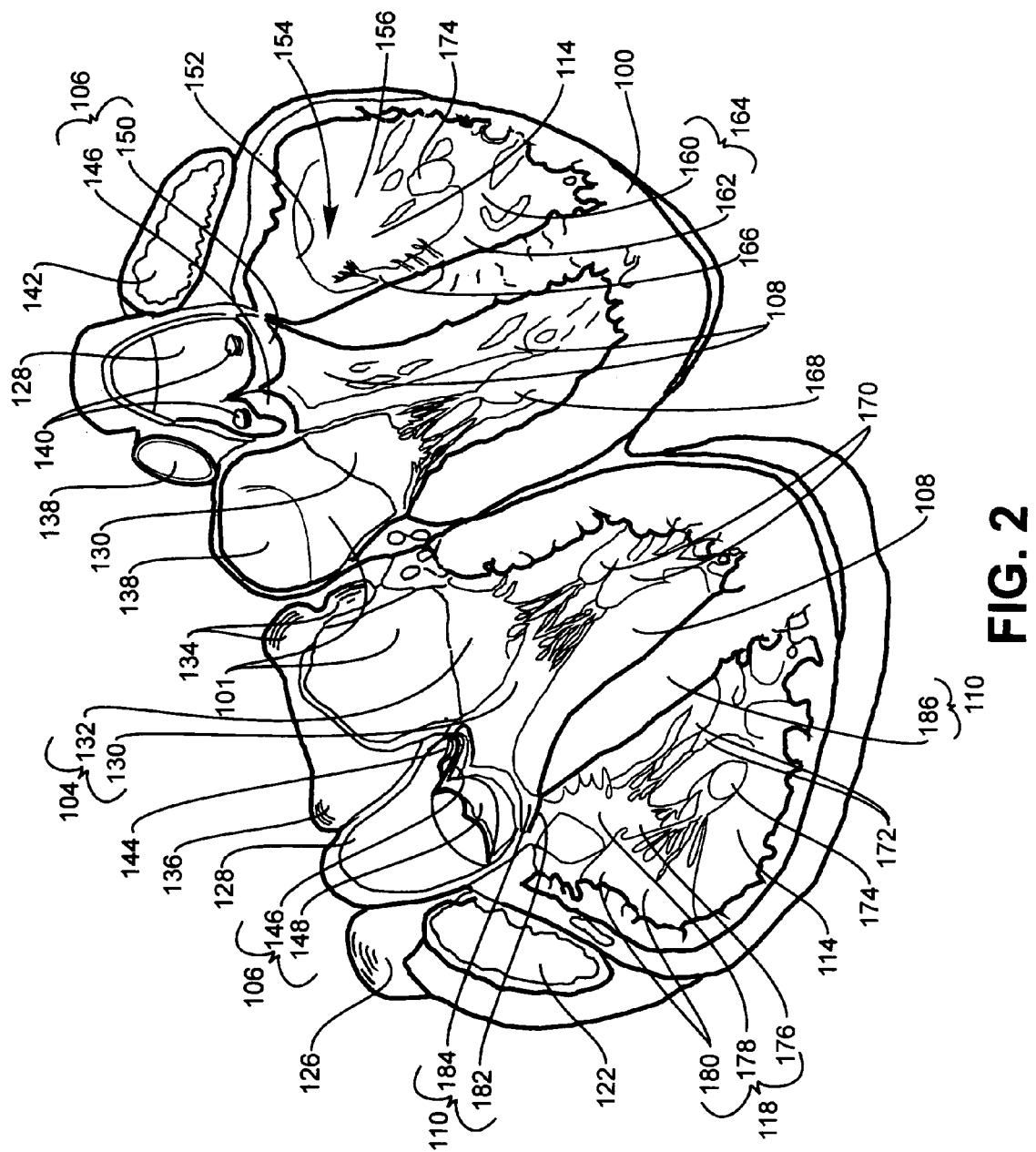
FIG. 2 schematically illustrates a vertical cross-section of the heart.

Referring to FIG. 2, a more detailed vertical cross-section of heart 100 is shown. Blood first collects in right atrium 122 from superior vena cava 126 or other veins. Right atrium 122 also includes right auricle 142. When right atrium 122 contracts, blood is sent through tricuspid valve 118 and into right ventricle 114. Tricuspid valve 118 is made up of three cusps: posterior cusp 176, septal cusp 178, and anterior cusp 180 (shown retracted). Right ventricle 114 has a number of muscles that contract to send blood out of right ventricle 114. Some of the muscles in right ventricle 114 include right anterior papillary muscle 174 (shown cut), and right posterior papillary muscle 172. Other parts of the anatomy of right ventricle 114 includes conus arteriosis 156, supra ventricular crest 152, and moderator band 160 and septal band 162 of septal marginal trabacula 164. The blood outflow to the pulmonary trunk is marked by arrow 154. Pulmonary trunk is shown as 138. The blood returning from the lungs returns by left pulmonary veins 134 and right pulmonary veins 136 where it collects in left atrium 101. Left atrium 101 also includes left auricle 138. When left atrium 101 contracts, blood is sent through mitral valve 104 which is made up of posterior cusp 132 and anterior cusp 130. Blood flows through mitral valve 104 and into left ventricle 108. Muscles in the left ventricle include left posterior papillary muscle 170, left anterior papillary muscle 168. Septum 110 separates left ventricle 108 from right ventricle 114. Septum 110 includes the muscular part of intraventricular septum 186, interventricular part of the membranous septum 182, and the atrial ventricular part of membranous septum 184. When left ventricle 108 contracts, blood is sent through aortic valve 106 which includes left semi-lunar cusp 146, posterior semi-lunar (non-coronary) cusp 148, and right semi-lunar cusp 150. Most of the blood flows through aortic valve 106 and into ascending aorta 128, although some of the blood is diverted into the openings of coronary arteries 140.

Figure 3:
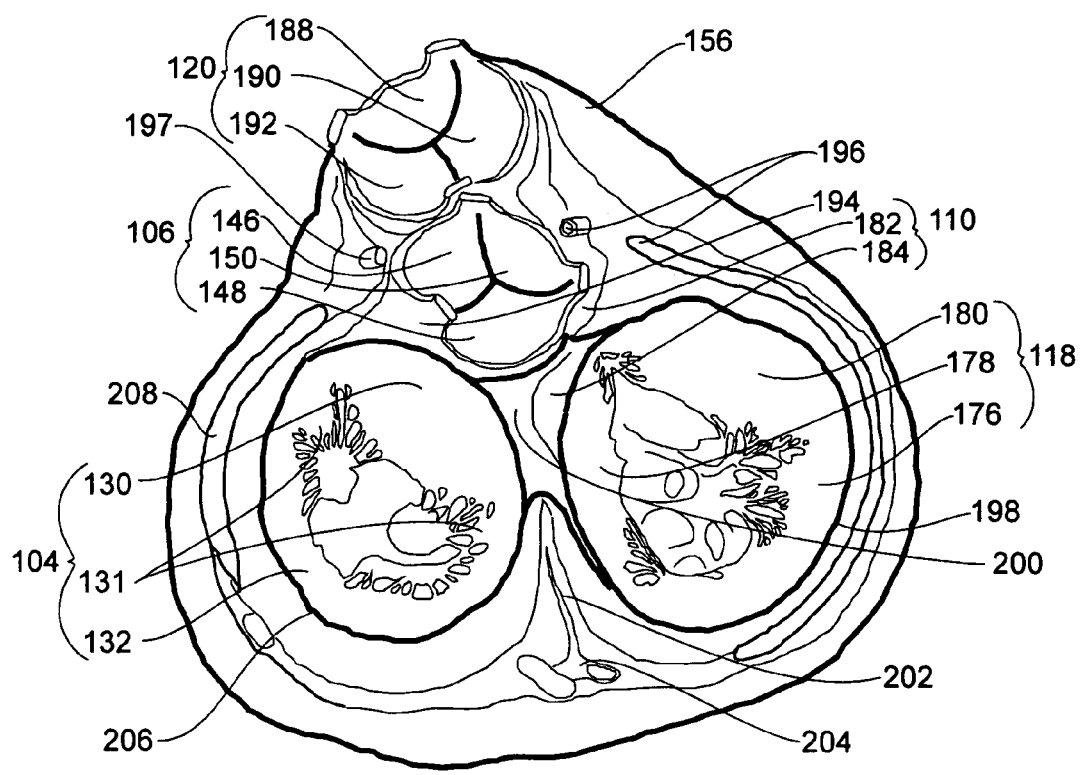
FIG. 3 schematically illustrates a horizontal cross-section of the heart in diastole showing valve operation.

Referring now to FIG. 3, is a horizontal cross-section of the heart showing the heart in diastole viewed from the base with the atria removed. Pulmonary valve 120 is shown in a closed position. Pulmonary valve 120 includes anterior semi-lunar cusp 198, right semi-lunar cusp 190, and left semi-lunar cusp 192. Aortic valve 106 is also shown in a closed position. Aortic valve 106 includes right (coronary) semi-lunar cusp 150, left (coronary) semi-lunar cusp 146, and posterior (non-coronary) semi-lunar cusp 148. The circumflex branch of the left coronary artery is labeled as reference number 208. Mitral valve 104 (between left atrium 101 and left ventricle 108) is shown in an open position. Mitral valve 104 includes anterior cusp 130, posterior cusp 132, and commissural cusps 131. There is also left fibrous ring 206 of mitral valve 104.

At the base of FIG. 3 (as viewed) is the posterior intraventricular branch of right coronary artery 204 and the atrial ventricular nodal branch of right coronary artery 202. In the middle of the heart is right fibrous trigone 200. Tricuspid valve 118 between the right atrium 122 and the right ventricle 114 is shown in an open position and includes anterior cusp 180, septal cusp 178, and posterior cusp 176. Surrounding tricuspid valve 118 is a right fibrous ring of tricuspid valve 198. Membranous septum 110 includes intraventricular part 182 (shown by a broken line) and atrialventricular part 184. Right coronary artery is shown as 196, and left coronary artery is shown as 197. Left fibrous trigone is shown as 194, and conus arteriosis is shown as 156.

Figure 4:
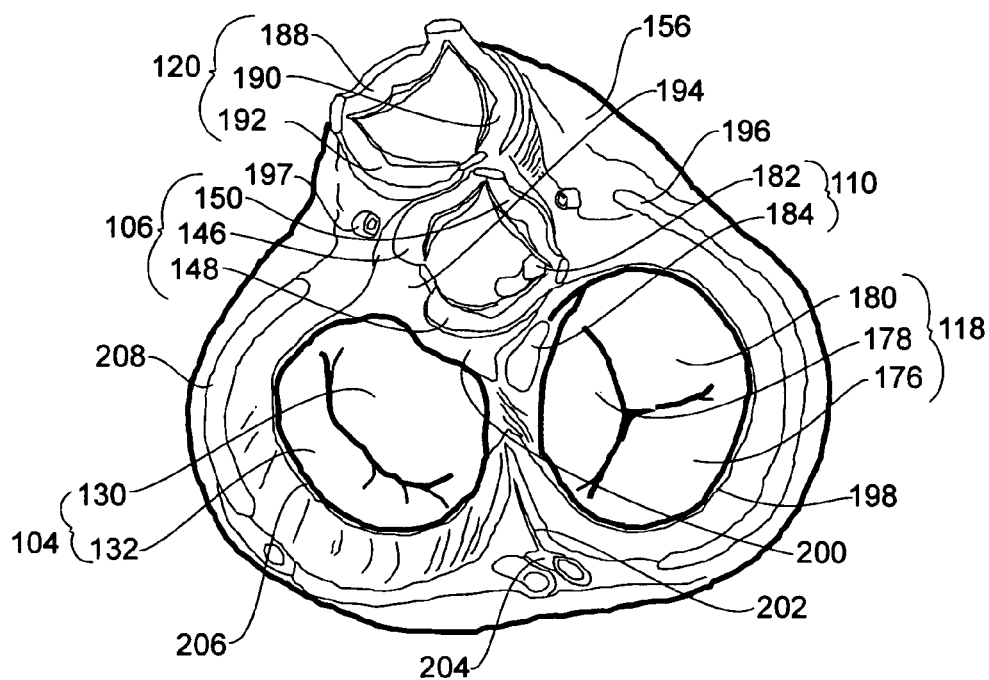
FIG. 4 schematically illustrates a horizontal cross-section of the heart in systole showing valve operation.

Referring to FIG. 4 is the heart in systole viewed from the base with the atria removed. All of the parts are essentially the same as in FIG. 3, however, in this figure, aortic valve 106 and pulmonary valve 120 are shown open and tricuspid valve 118 and mitral valve 104 are shown closed. Again, pulmonary valve 120 has anterior semi-lunar cusp 188, right semi-lunar cusp 190, and left semi-lunar cusp 192. Aortic valve 106 is made up of right (coronary) semi-lunar cusp 150, left (coronary) semi-lunar cusp 146, and posterior (non-coronary) semi-lunar cusp 148. Mitral valve 104 is shown with anterior cusp 130 and posterior cusp 132 surrounded by left fibrous ring 206. Tricuspid valve 118 is shown with anterior cusp 180, septal cusp 178, posterior cusp 176, surrounded by right fibrous ring of tricuspid valve 198. Right coronary artery is shown as 196 with atrial ventricular branch 202 of right coronary artery 196 and posterior interventricular branch 204 of right coronary artery 196 showing. Left coronary artery 197 is also shown. Other parts of the heart shown in FIG. 4 are the same as those shown in FIG. 3.

Figure 5:
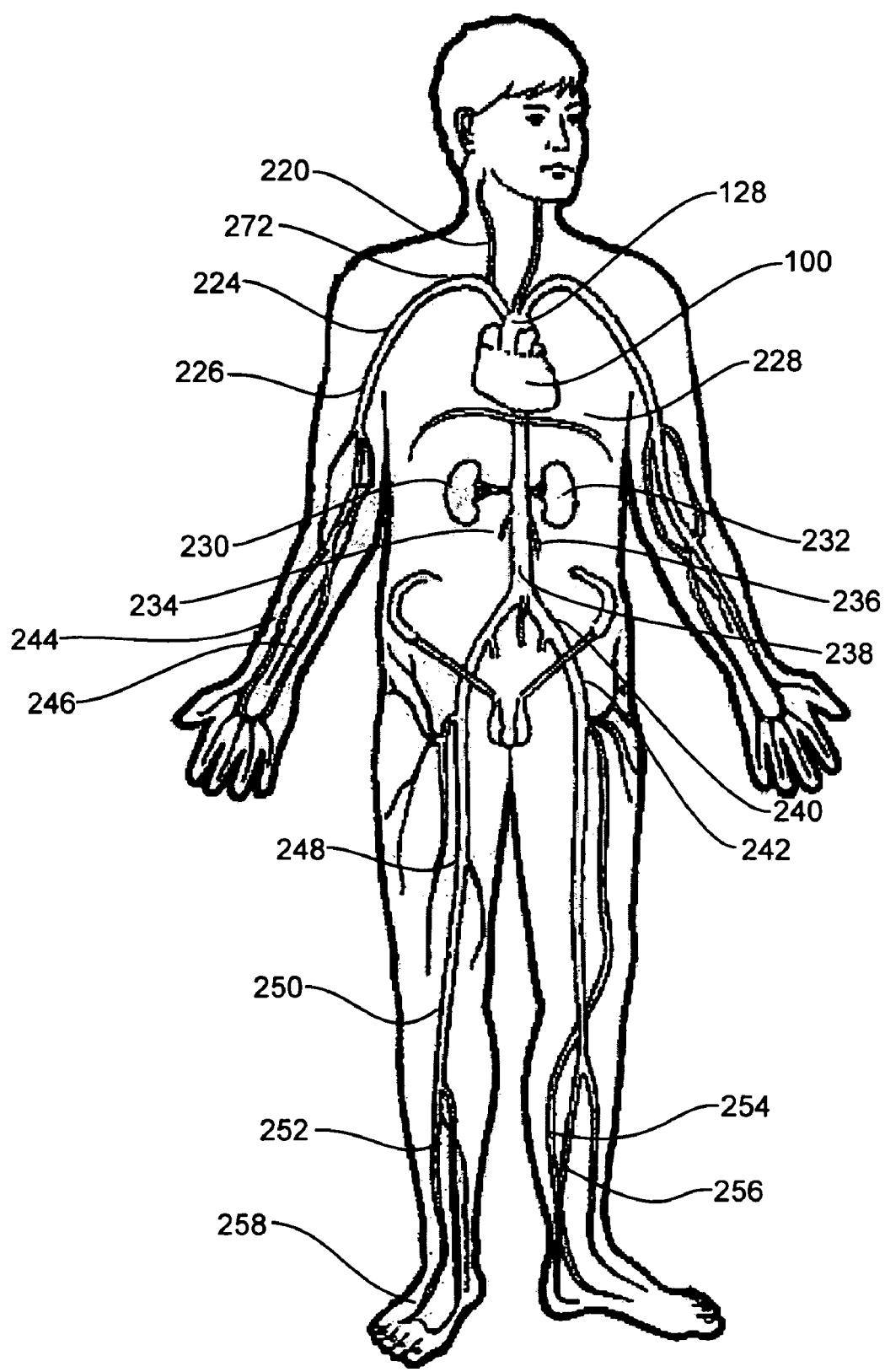
FIG. 5 schematically illustrates major arteries of the body.

Referring now to FIG. 5, which schematically illustrates major arteries of the body. The oxygenated blood of the body originates in heart 100 and is pumped by the left ventricle (not shown) into aorta 128. From aorta 128, the blood branches throughout the rest of the body. A first branch, subclavian artery 222 feeds axillary artery 224 which turns into brachial artery 226. Brachial artery 226 in turn feeds radial artery 244 and ulnar artery 246. Another branch off of aorta 128 is common carotid artery 220. Diaphragm 228 is also shown under heart 100. The lower branch of aorta 238 feeds blood to kidneys 230 through renal artery 232. There are also two branches off of the lower branch of aorta 238, the first, superior mesenteric artery 234, and the second, inferior mesenteric artery 236. Lower branch of aorta 238 splits and feeds common iliac artery 240 for both legs. The common iliac artery in turn branches into external iliac artery 242 and femoral artery 248. One of the branches of femoral artery 248 is popliteal artery 250 which branches into anterior tibial artery 252, posterior tibial artery 256, and dorsalis pedis artery 258. Peroneal artery 254 branches off of external iliac artery 242.

Figure 6:
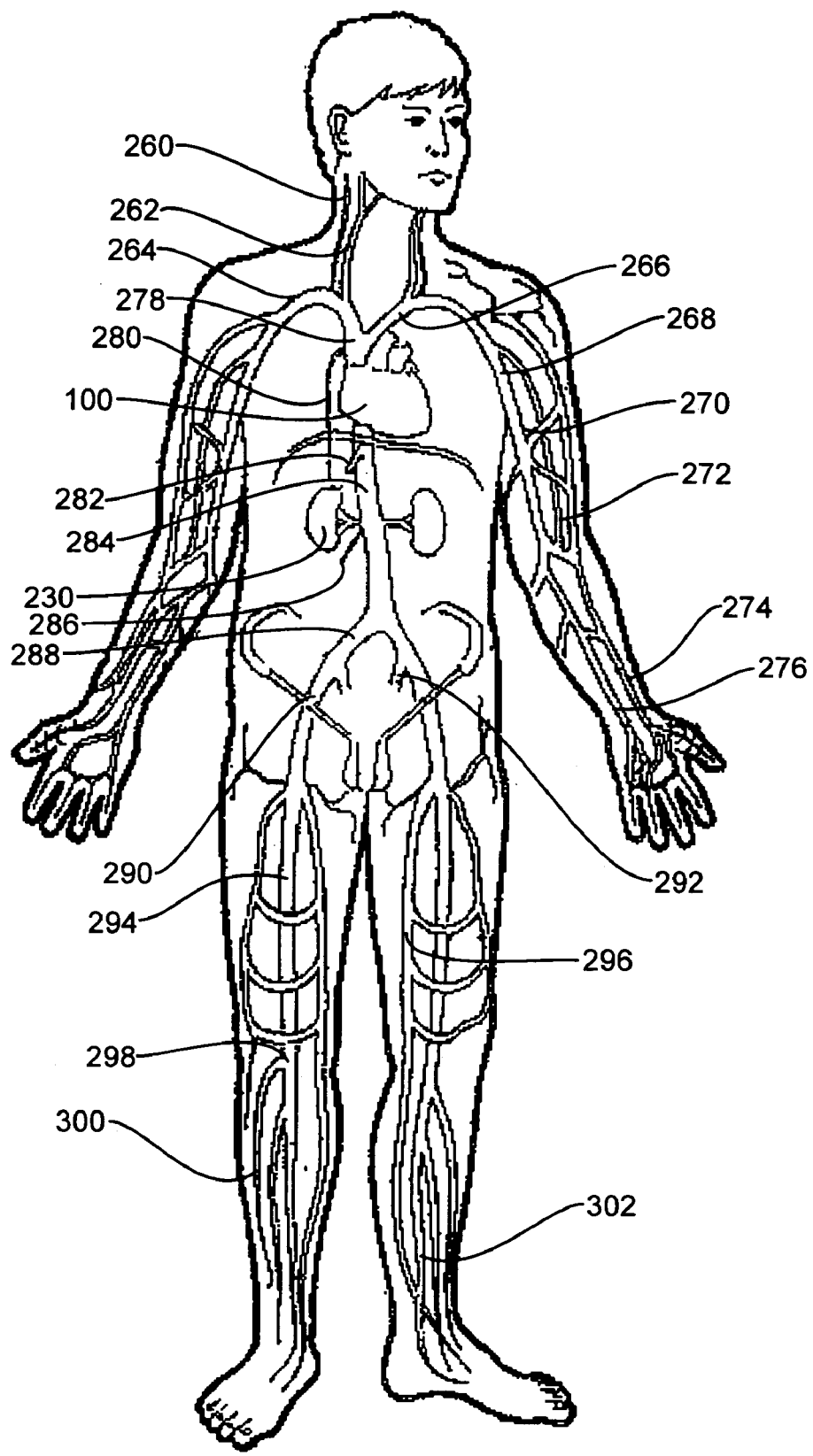
FIG. 6 schematically illustrates major veins of the body.

Referring now to FIG. 6, which schematically illustrates major veins of the body. The deoxygenated blood returns to heart 100 through the venous system. Some blood returning from the legs flows into posterior tibial vein 302, and anterior tibial vein 300, which feed into popliteal vein 298, and flows into femoral vein 294. Another vein in the legs is great saphenous vein 296 which also feeds into femoral vein 294. Blood then flows into either internal iliac vein 292 or external iliac vein 290 which then flow into common iliac vein 288 to return to heart 100 via inferior vena cava 284. Blood returning from kidneys 230 flows through renal vein 286 and then to inferior vena cava 284 which mixes with the blood coming from common iliac vein 288. Other branches feeding into inferior vena cava 284 include hepatic vein 282. Blood returning from the left arm flows into ulnar vein 276, radial vein 274, or brachial vein 272, or basilic vein 270, and flows into axillary vein 268. Blood flows from axillary vein 268 into left innominate vein 266 which flows into superior vena cava 278. (A similar arrangement can be found in the right arm.) Blood also flows into superior vena cava 278 from right subclavian vein 264, and from external jugular vein 260 and internal jugular vein 262.

Delivery catheter 320 is shown in FIGS. 7, 8, and 9. Delivery catheter 320 includes flexible shaft 322 having distal end 324, proximal end 326 and delivery lumen 328 extending therebetween. In one embodiment, shaft 322 is at least about 50 cm long, and in another embodiment, at least about 60 cm long, between proximal end 326 and distal end 324, so that distal end 324 may be positioned in the coronary sinus with proximal end 326 extending out of the patient through a puncture in a peripheral vein, such as femoral vein. Shaft 322 is made of a material such that it is sufficiently flexible to navigate this path without difficulty. In one embodiment, shaft 322 is made of a biocompatible polymer such as a polyether block amide resin, for example, PEBAX, a registered trademark of Atochem, with a durometer in a range of about 50 to about 72 Shore D. In another embodiment, a portion, including the entire portion, of shaft 322 is radiopaque to permit fluoroscopic observation thereof to facilitate positioning. Radiopaque markers may be applied to the shaft near distal end 324, or a filler such as barium sulfate may be added to the polymeric material used to form shaft 322.

In order to allow percutaneous introduction of delivery catheter 320 in a peripheral vein, in one embodiment, shaft 322 will have an outer diameter OD of no more than about 5.0 mm from distal end 324 to at least about 30 cm proximal thereto, and in another embodiment, to at least about 50 cm proximal thereto.

In one embodiment, delivery catheter 320 is adapted for introduction through a commercially-available 9 French or 10 French introducer sheath or a suitably sized guide catheter, or by feeding over a guidewire, or for introduction by surgical cut-down into a comparably-sized peripheral vein. In one embodiment, guide catheter is adapted to be fed into femoral vein 294, then to external iliac vein 290, then to common iliac vein 288, to inferior vena cava 284 (see FIG. 6), then into right atrium 122, and into coronary sinus 586 (see FIG. 11), and can then be fed further into venus system on exterior of heart (not shown). In another embodiment, guide catheter is adapted to be fed into external jugular vein 260 or internal jugular vein 262, into superior vena cava 278 (see FIG. 6), and then into right atrium 122 and into coronary sinus 586, where guide catheter may stay in coronary sinus 586, or be fed further into the venus system on exterior of the heart (see FIG. 11). In one embodiment, a suitable guide catheter is described in a co-pending patent application Ser. No. 10/293,535 filed on Nov. 12, 2002 (assigned to Guidant Corporation); the co-pending patent application filed on Nov. 12, 2002 is herein incorporated by reference in its entirety. The guide catheter disclosed in the co-pending patent application filed on Nov. 12, 2002 may be inserted into femoral vein 294 (see FIG. 6), which guide catheter has a first convex curved portion, a concave curved portion distal to the first convex curved portion, and a second convex curved portion distal to the concave curve portion. Other suitable catheters include the Viking Opima Line™ (a trademark of Guidant Corporation), the ACS Viking™ line of guide catheters (a trademark of Guidant Corporation), and the ACS RAD Curve™ line of guide catheters (a trademark of Guidant Corporation). Other suitable guide catheters are manufactured by Guidant Corporation. Suitable guide catheters include EasyTrak® guiding catheters, Rapido™ guiding catheters, and telescoping guide catheters, for example, CS-MP REF 7300 and CS-IC 90 REF 666776-101.

Soft tip 330 (of for example, PEBAX with a durometer of 20 to 30 Shore D) is bonded to distal end 324 of shaft 322 to reduce the risk of trauma to the coronary sinus or other tissue.

Delivery lumen 328 extends from fitting 332 at proximal end 326 through shaft 322 and through soft tip 330 to outlet port 392 in the distal end of soft tip 330. Side holes 334 in communication with delivery lumen 328 may also be provided near distal end 324 of shaft 322 as shown in FIG. 8. In one embodiment, delivery lumen 328 preferably has a cross-sectional area no less than about 4 mm$^2$ at any point between proximal end 326 and outlet port 392 to facilitate delivery of treatment agent at sufficient flow rates while keeping the pressure at which the treatment agent is delivered low enough to avoid excessive hemolysis if there is a blood component of the treatment agent, as described more fully below. In one embodiment, the inner diameter (ID) of delivery lumen 328 is at least about 2.8 mm, and height H1 is at least about 1.8 mm.

Catheter 320 is provided with balloon 347 on distal end 324 of catheter 320 which is adapted to occlude the coronary sinus or another vessel when inflated. In one embodiment, balloon 347 is a biocompatible polymer such as a polyether block amide resin, for example, PEBAX® (a registered trademark of ATOCHEM CORPORATION, PUTEAUX, FRANCE). In another embodiment, balloon 347 is a biocompatible polymer blend of polyurethane and silicone, for example PERSOL. In one embodiment, balloon 347 has an inflated diameter range of about 4 mm to about 9 mm, an uninflated diameter of about 3 mm, and a working length of about 6 mm.

In one embodiment, balloon 347 may be located at least about 15 mm from distal end 324 of shaft 322 so that, during positioning, if balloon 347 is pulled out of the coronary sinus, there is sufficient length of shaft 322 distal to the balloon that will remain in the coronary sinus to eliminate the need to relocate distal end 324 in the coronary sinus.

In one embodiment, balloon 347 is formed by dipping a mandrel in liquefied polymer and curing as needed. Balloon 347 may be attached to shaft 322 by, for example, heat welding or an adhesive.

Inflation lumen 336 extends through shaft 322 and is in communication with the interior of balloon 347 through opening 337. Near proximal end 326, inflation lumen 336 is connected to inflation extension tube 338 attached to shaft 322 having fitting 340 at its proximal end for attachment to an inflation fluid delivery device. In one embodiment, inflation lumen 336 is configured to allow delivery of inflation fluid or gas at a sufficient rate to fully inflate balloon 347 in about two seconds. In another embodiment, inflation lumen 336 has a height H2 of about 0.5–0.9 mm and a width W of about 0.9–1.3 mm. Inflation lumen 336 may alternatively be a coaxial lumen around shaft 322, enclosed by a separate tubular member (not shown).

Optionally, pressure relief valve 341 may be connected to inflation extension tube 338 to prevent overinflation of balloon 347, which might damage the tissue of the coronary sinus or another vessel. Pressure relief valve 341 is configured to open and relieve fluid pressure from inflation lumen 336 when balloon 347 exceeds the maximum desired inflated diameter, e.g., about 9 mm. This may be accomplished by pre-inflating balloon 347 to the maximum inflated diameter without pressure relief valve 341 mounted to the delivery catheter, thereby plastically deforming balloon 347 to its fully inflated size. Balloon 347 is then collapsed onto the shaft by applying a vacuum to inflation lumen 336, and pressure relief valve 341 is mounted to inflation extension tube 338. In use, when delivery catheter 320 is positioned in the coronary sinus, inflation of balloon 347 to the desired inflated size will require relatively low pressure, e.g. less than about 0.5–2.0 psi. However, once the maximum inflated size is reached, the pressure will increase significantly, causing pressure relief valve 341 to open, thus preventing overinflation of balloon 347. A suitable pressure relief valve 341 is available from, for example, Smart Products, Inc. of San Jose, Calif., under the name "Luer Check Valve."

In another embodiment, balloon 347 may be self-inflating, wherein the treatment agent itself acts as the inflation fluid for balloon 347, eliminating the need for a separate inflation lumen 336 in shaft 322. In this embodiment, delivery lumen 328 communicates with the interior of balloon 347 in such a way that balloon 347 will inflate fully to occlude the coronary sinus only during delivery of treatment agent. For example, a fluid path between delivery lumen 328 and balloon 347 may be provided such that all or a major portion of the treatment agent delivered through delivery lumen 328 first enters the balloon to cause balloon 347 to inflate, before treatment agent flows into the coronary sinus through outlet holes in shaft 322 distal to balloon 347, or through outlet holes in the balloon itself. One way to accomplish this is by a reduction in the diameter of the lumen distal to balloon 347 such that a sufficient head pressure is established to inflate balloon 347 and administer a treatment agent from shaft 322.

Figure 10:
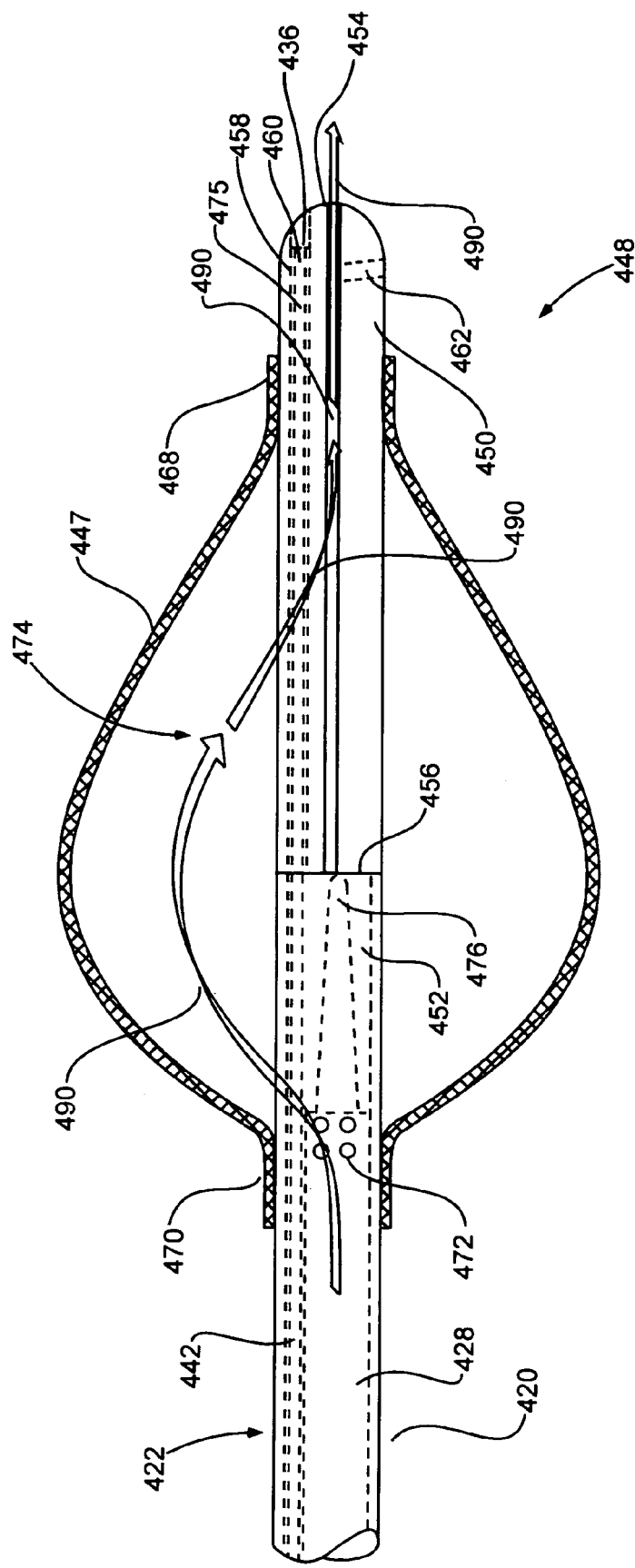
FIG. 10 schematically illustrates a sectional view of a catheter with a self inflating balloon.

A suitable self-inflating balloon configuration is illustrated in FIG. 10.

Pressure lumen 342 may also be provided in shaft 322 which opens at pressure port 344 on side wall of shaft 322 near distal end 324, or in soft tip 330 as illustrated. Pressure lumen 342 is connected to extension tube 346 attached (e.g., via adhesive) to shaft 322 near proximal end 326 and includes fitting 348 at its proximal end suitable for connection to pressure monitoring equipment. In this way, pressure in the coronary sinus distal to balloon 347 may be monitored during treatment agent delivery to ensure that pressure within the coronary sinus is maintained at a safe level. Pressure relief valve, like relief valve 341 connected to inflation extension tube 338, may also be connected to delivery lumen 328 to ensure that treatment agent pressure does not exceed a predetermined level, avoiding hemolysis in the blood component of the fluid and/or protecting the coronary sinus from excessive infusion pressure. In one embodiment, pressure in the range of about 0 to about 5 mmHg could be measure at port 344.

As shown in FIG. 8, distal portion of shaft 322 may include first bend 350 and second bend 352, which facilitate the placement of distal end 324 in the coronary sinus. In one embodiment, second bend 352 may be a distance L2 of about 3 mm–10 mm from distal end of soft tip 330, and first bend 350 may be a distance L1 of 20 mm–40 mm proximal to second bend 352. First and second bends 350, 352 may subtend various angles depending upon patient anatomy and surgeon preference. In one embodiment configuration, first bend 350 subtends an angle A of between about 20° and about 70° relative to the longitudinal axis of proximal portion 354 of shaft 322. In another embodiment, second bend 352 may subtend an angle B of about 30° to about 40° relative to mid-portion 356 of shaft 322.

A liquid containing a treatment agent or drug, e.g., a caroporide solution, may be introduced into proximal end 326 of catheter 320, which extends outside of the patient, under sufficient pressure so that the fluid containing the treatment agent can be forced to pass through the coronary sinus, through the capillary beds (not shown) in the patient's myocardium, and optionally through coronary arteries (not shown) and ostia associated with the respective coronary arteries (not shown) into the ascending aorta (not shown).

In one embodiment, balloon 347 on the distal extremity of catheter 320 is inflated to occlude the coronary sinus to prevent fluid loss into the right atrium. A liquid containing a treatment agent such as adenosine is directed through catheter 320 into the coronary sinus and the pressure and volumetric flow rate of the treatment agent within the coronary sinus are maintained sufficiently high (e.g. at least 100 ml/min at about 40 mm Hg) so that the treatment agent will pass through the coronary veins, and reaching the capillary beds, and optionally on to the coronary arteries (not shown) and out the ostia (not shown).

Treatment agent is delivered through delivery catheter 320 at a flow rate sufficient to maintain desired treatment by periodic or continual infusions. However, treatment solution pressure within the coronary sinus should be less than about 50 mm Hg to avoid tissue damage. In one embodiment, the treatment agent is a mixture of blood and a treatment agent such as an antioxidant, in one embodiment at a ratio or four parts blood to one part antioxidant solution (by volume). This antioxidant solution may be mixed into oxygenated blood.

The treatment agent may be directed to port 332 on proximal end of delivery catheter 320, and delivered to the coronary sinus, or another vessel, in one embodiment at a flow rate of at least about 100 ml/min. and in another embodiment, at about 200 ml/min. If treatment agent includes a blood component, the pressure required to pump the treatment agent through the lumen of the delivery catheter ("pump pressure") should not exceed 300 mmHg so as to avoid excessive hemolysis of the blood component. Treatment agent flow through delivery catheter 320 is maintained on a periodic basis, e.g., about every 15–30 minutes for 2–4 minutes, so long as the heart is to remain under treatment.

A suitable self-inflating balloon configuration is illustrated in FIG. 10. FIG. 10 illustrates the structure and operation of self inflating balloon 447 and flow tip 448. Pear shaped balloon 447 tapers gradually from its widest diameter to form distal circular cuff 468, and tapers more quickly from its widest diameter to form proximal circular cuff 470. Proximal cuff 470 coaxially receives catheter body 422 and is attached thereto to form a fluid tight seal between cuff 470 and catheter body 422. Distal cuff 468 coaxially receives and attaches to flow tip 448.

Plurality of radial holes 472 extend through body of catheter 422 from within infusion lumen 428, proximal of flow tip base plug 452, into interior space 474 enclosed by balloon 447. Thus the flow of treatment agent through catheter 420 shown by arrows 490 exits infusion lumen 428 through holes 472, enters balloon interior 474, flows into flow channels 458 and exits each flow channel 458 through its side exits 462, or distal exits 454. The aggregate cross sectional area of holes 472 filling balloon interior 474 exceeds the aggregate cross sectional area of flow channels 458 draining balloon interior 474, providing a positive pressure within balloon interior 474 to keep balloon 447 inflated while the treatment agent flows through catheter 420.

Pressure monitoring lumen 442 extends through one of open channels 458 by means of extension tube 475. Extension tube 475 extends from flow tip body 450, where pressure monitoring lumen 442 exits flow tip body 450, through one of flow channels 458, and terminates proximally adjacent flow channel distal exit (not shown), to form pressure lumen distal opening 436. The pressure monitoring equipment (not shown) is thus in pressure communication with the inside of the coronary sinus or another vessel in which pressure lumen distal opening 436 is located. Because the pressure lumen distal opening 436 is recessed into the flow channel 458, there is less chance of it becoming occluded by the wall of the coronary sinus.

Also note that stylet well 476 can coaxially sink into base plug 452 of nozzle 448 for receiving a stylet (not shown), and providing additional reinforcement at distal end 456 of catheter body 422 where the stylet (not shown) impacts base plug 452 of nozzle 448.

Figure 11:
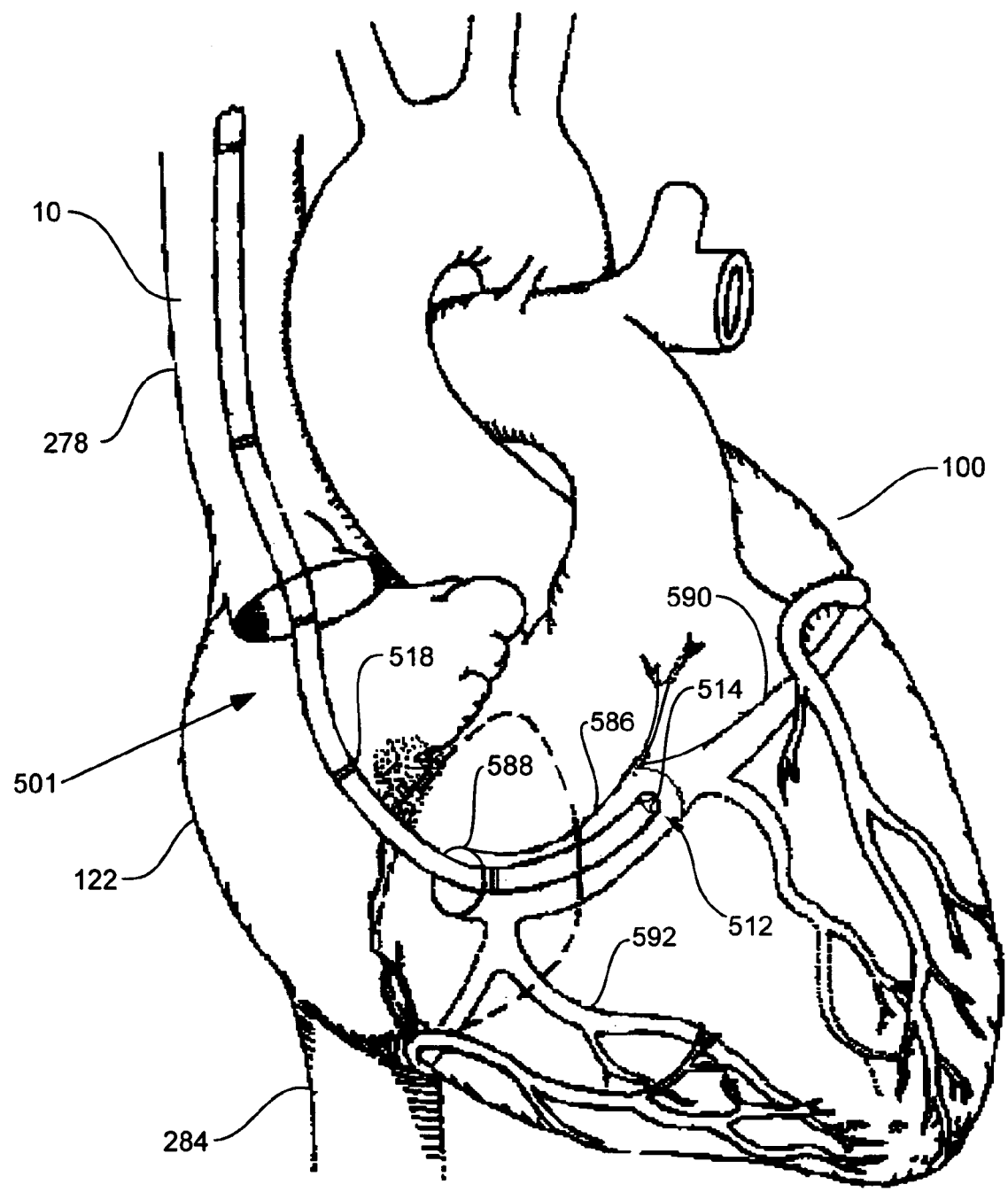
FIG. 11 schematically illustrates the placement of a catheter in the coronary sinus.

FIG. 11 depicts catheter 501 position within heart 100. Catheter 501 may be inserted through a percutaneous venus entry, such as through femoral vein 294, and tip 512 is guided through right atrium 122 into coronary sinus 586. Blood drains into right atrium 122 via superior vena cava 278 and interior vena cava 284, and from coronary sinus 586 via coronary sinus ostium 588. Moreover, blood drains from the myocardium to coronary sinus 586 via great cardiac vein 590 and small cardiac vein 592.

Tip 512 having port 514 is inserted into coronary sinus 586 to a depth from about 0 to about 4 inches (0 to about 10.2 cm) from coronary sinus ostium 588. Optionally, markers 518 may be provided on catheter 501 and optionally spaced about 2 inches apart along catheter 501; in one embodiment, markers 518 are radiopaque.

Figure 12:
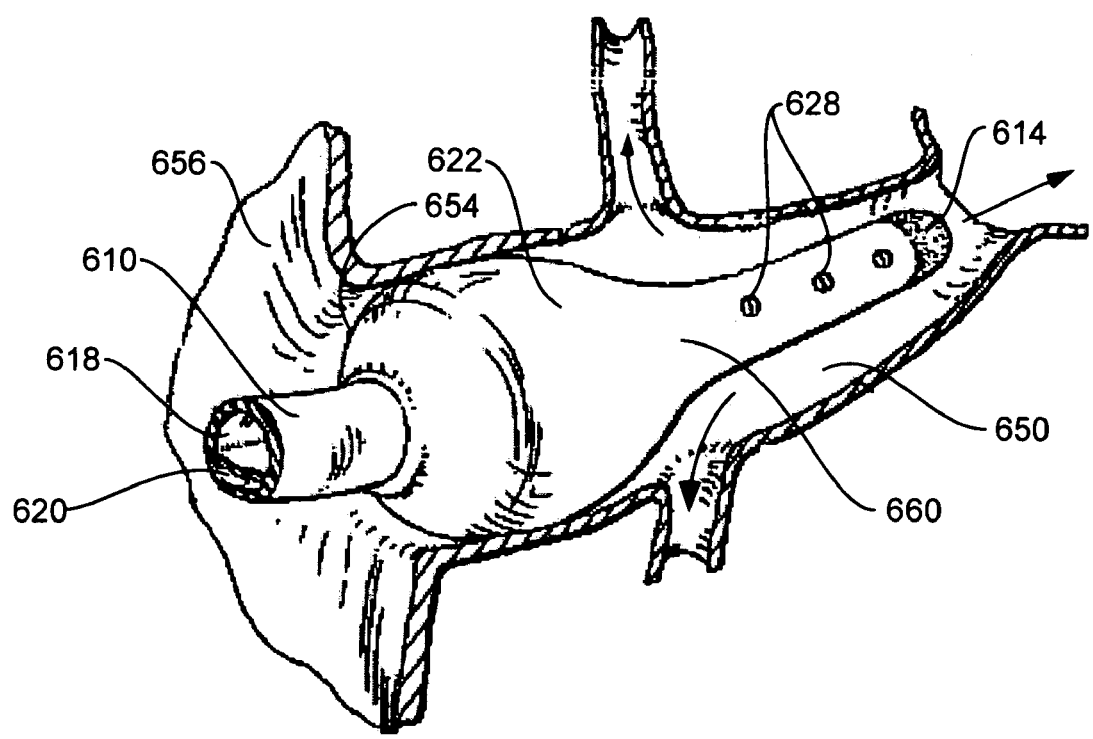
FIG. 12 schematically illustrates a partial cross-sectional perspective view of a catheter within the coronary sinus.

FIG. 12 illustrates distal end 660 of catheter 610 within coronary sinus 650. Catheter 610 has tip 614 at distal end 660, and plurality of lumen outlets 628 proximal to tip 614. Balloon 622 is shown occluding coronary sinus 650 and coronary sinus ostium 654 adjacent to right atrium wall 656. In this embodiment, a self-inflating balloon is shown with infusion lumen 618 through which a treatment agent flows and inflates balloon 622 then flows out of lumen outlets 628. Pressure sensing lumen 620 is also provided. In another embodiment, a third lumen was provided (not shown) to inflate balloon 622 when balloon 622 is not self-inflating.

In one embodiment, balloons 347, 447, and/or 622 are made from a polymer material. In one embodiment, the polymer material is synthetic or natural latex. In another embodiment, the polymer material is a polyether block amide resin, a polyetheramide, or a plasticiser free thermoplastic elastomer, for example, PEBAX®, a registered trademark of Atochem. In another embodiment, balloons 347, 447, and/or 622 are made from a blend of different types of PEBAX®.

In one embodiment, balloons 347, 447, and/or 622 are made from a styrenic block copolymer (SBC), or a blend of SBC's. Suitable SBC's are sold under the tradename Kraton Polymers® a registered trademark of Shell Oil Company.

In another embodiment, the polymer material is a polyurethane-silicone blend, for example, PERSOL. In another embodiment, the polymer is a homopolymer of an olefin. In another embodiment, the polymer is a co-polymer of an olefin and one or more other material(s). In one embodiment, balloons 347, 447, and/or 622 have a coating applied to its inside and/or outside surface, for example, a hydrophilic coating.

In one embodiment, balloons 347, 447, and/or 622 are made of a material that minimizes allergic reactions and/or provides improved control of expansion diameter. In one embodiment, balloons 347, 447, and/or 622 can be used in a vessel having a diameter range of about 4 mm to about 9 mm diameter. In one embodiment, balloons 347, 447, and/or 622 are thicker distally and thinner proximally. In one embodiment, balloons 347, 447, and/or 622 have a conical shape.

In one embodiment, a balloon (for example balloons 347, 447, 622, 1347, 2147, and/or 2247) may be placed in the coronary sinus or a cardiac vein, for example, the great cardiac vein, a branch of the great cardiac vein, the middle cardiac vein, or the small cardiac vein. In this embodiment, the coronary sinus or the cardiac vein may be elastic in nature, so the balloon may prevent vessel hematomas or occlusion of adjacent coronary artery by functioning as a sealer, and not a dilator. In one embodiment, the balloon is very compliant, achieving occlusion at low pressure for a range of vessel sizes. For example, a diameter of the coronary sinus may range from about 6.5 to about 11 mm, a diameter of the great cardiac vein may range from about 4.0 to about 7.5 mm, and the diameter of a branch of the great cardiac vein may range from about 2.5 to about 5.0 mm.

In another embodiment, a balloon (for example balloons 347, 447, 622, 1347, 2147, and/or 2247) may be placed in the coronary sinus or a cardiac vein, for example, the great cardiac vein, a branch of the great cardiac vein, the middle cardiac vein, or the small cardiac vein, to occlude the vessel prior to the infusion or retroinfusion of a fluid or treatment agent. In this embodiment, the balloon is able to extend if the vessel is enlarged during the infusion or retroinfusion and maintain occlusion of the vessel.

In another embodiment, a balloon (for example balloons 347, 447, 622, 1347, 2147, and/or 2247) may be made from or comprise a polyether block amide, a polyetheramide, and mixtures thereof. In another embodiment, the balloon (for example balloons 347, 447, 622, 1347, 2147, and/or 2247) may be made from or comprise a polymer having a structure of a regular linear chain of rigid polyamide segments interspaced with flexible polyether segments. In another embodiment, the balloon (for example balloons 347, 447, 622, 1347, 2147, and/or 2247) may be made from or comprise a polymer or a mixture of two or more of the polymers having the tradename PEBAX® (a registered trademark of ATOCHEM), for example Pebax 63D and 55D, or for example one or more Pebax polymers having a Shore D hardness less than 70D. In another embodiment, the balloon (for example balloons 347, 447, 622, 1347, 2147, and/or 2247) may be made from or comprise a polymer or a mixture of two or more of the polymers represented by the formula:

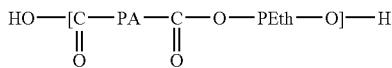

(Where PA represents a polyamide segment, and PEth represents a polyether segment.)

In another embodiment, a balloon (for example balloons 347, 447, 622, 1347, 2147, and/or 2247) may operate at a pressure of about 0.5 to about 5 atmospheres. In another embodiment, the balloon may achieve a growth rate greater than about 40%. In another embodiment, the balloon may have an expanded or unexpanded outer diameter between about 1.5 and about 18 mm. In another embodiment, the balloon may have a double wall thickness between about 0.0006 and about 0.0028 inches. In another embodiment, the balloon may have a minimum hoop strength of at least about 23,000 psi. In another embodiment, the balloon may be either heat bonded (for example with a laser), or attached with an adhesive to an occlusion device (for example a catheter).

Figure 23:
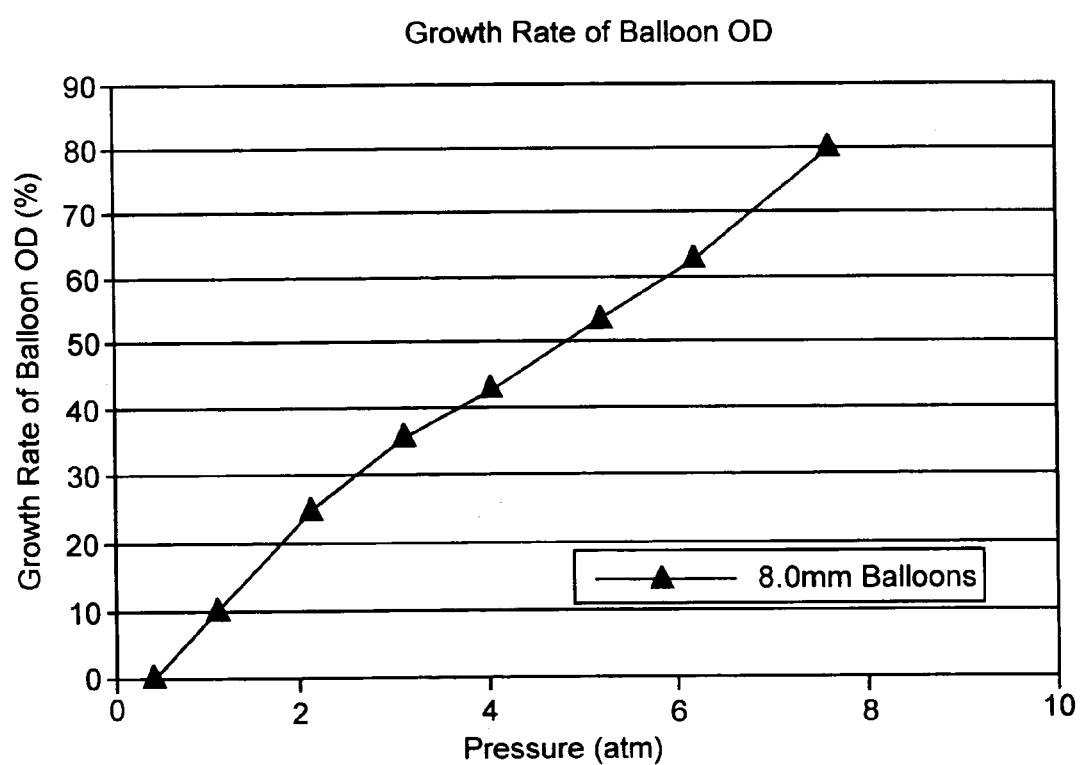
FIG. 23 illustrates a balloon outside diameter growth rate.

Referring now to FIG. 23, there is illustrated a balloon outside diameter growth rate. In this figure, a test was conducted on 8 mm balloons (uninflated outside diameter), and the balloons were inflated, and the growth rate was plotted as a function on the inflation pressure.

In one embodiment, balloon sizing is controlled by monitoring venous pressure waveform change distal to balloon 347, 447, and/or 622. In one embodiment, inflation of balloon may be continued until waveform becomes ventricularized.

Figure 13:
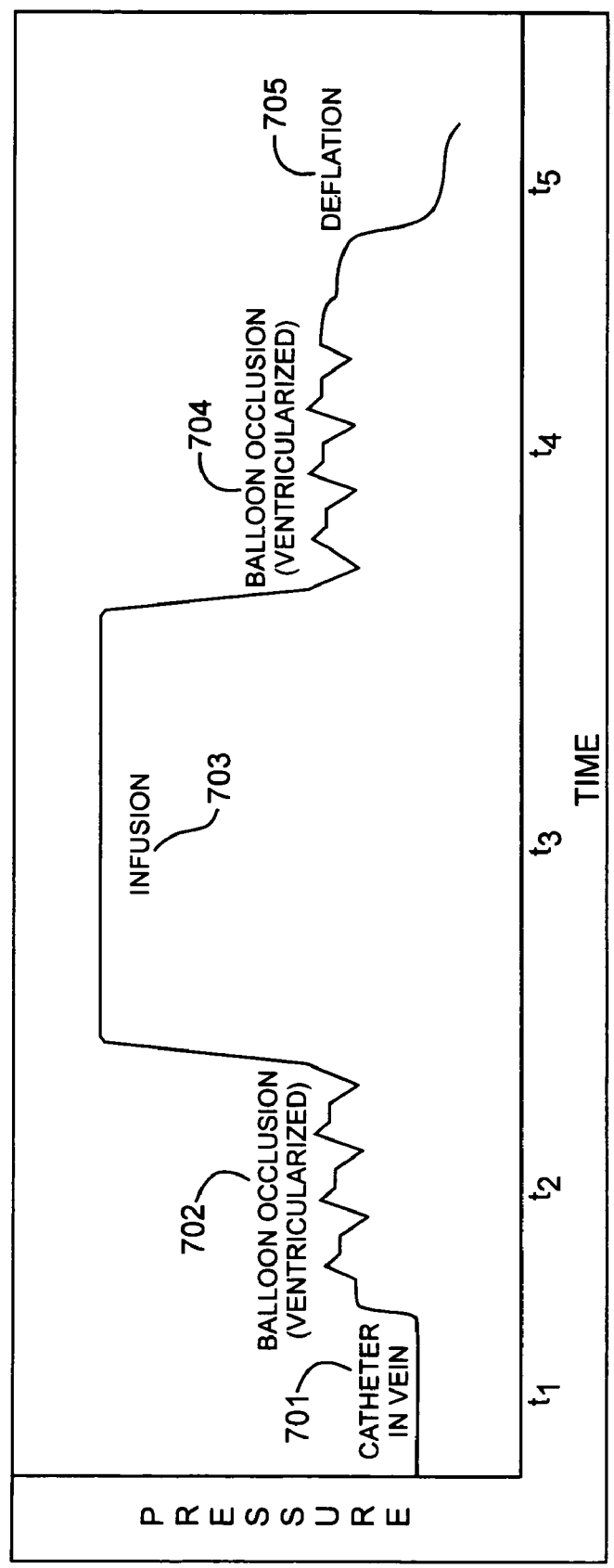
FIG. 13 illustrates a graph of blood vessel pressure over time.

FIG. 13 illustrates a graph showing pressure distal to balloons 347, 447, and/or 622 in vessel as a function of time. Reference numeral 701 illustrates time t1 where catheters 320, 422, 501, and/or 610 are located in the coronary sinus or another vessel. Reference numeral 702 corresponds to time t2 where balloons 347, 447, and/or 622 are inflated to occlude the coronary sinus or another vessel. When the coronary sinus or another vessel is occluded, for example until when the coronary sinus or another vessel has a pressure waveform that becomes ventricularized. Reference numeral 703, corresponding to time t3 is the infusion period, where a liquid is introduced into the vessel at a relatively higher pressure distal to balloons 347, 447, and/or 622. At the conclusion of the infusion period, t3, is time t4 referred to by reference numeral 704, is a period of lower pressure following infusion, when the coronary sinus or another vessel is still occluded by balloons 347, 447, and/or 622. Reference numeral 705, referring to time t5, is the period when balloons 347, 447, and/or 622 are deflated, the catheter may be removed and blood flow can resume in the coronary sinus or another vessel.

In one embodiment, the algorithm illustrated in FIG. 13 allows for an efficient drug infusion from a vein to tissue to be treated with the possibility of "hands-off" operation. In one embodiment, when the pressure waveform changes to a "ventricularized" waveform of venous pressure, a balloon-sizing indicator notifies the operator or control system to stop balloon inflation. After balloon inflation has been stopped, a pressure sensor can measure the infusion pressure needed for an effective therapeutic dosage of a liquid containing a treatment agent. Infusion of a treatment agent can be accomplished with auto-infusion with a controller, or by an operator manually.

Suitable treatment agents to be used with catheters 320, 422, 501 and/or 610 include a liquid carrying one or more treatment agents. In one embodiment, the liquid includes one or more drugs and/or treatment agents. In another embodiment, liquid includes one or more drugs and/or treatment agents used to prevent reperfusion injury. In one embodiment, the liquid includes one or more antibodies, for example, the antibodies against CD 11/18, P-selectin, L-selectin, ICAM, and/or VCAM. In another embodiment, the liquid includes IGF-I, estrogen, and/or GIK solution. In another embodiment, the liquid includes drugs like adenosine or its isoforms, Na/H exchangers, and/or Na/K exchangers. In another embodiment, the liquid can include cells, for example, cardiomyocites and/or multi-potent or ologo-potent cells like stem cells and/or progenitor cells. In another embodiment, the liquid includes angiogenic cells, and/or other types of structural cells like skeletal or smooth muscle cells. In another embodiment the liquid includes biological agents and/or genes, for example, VEGF, FGF, and/or HGF. In another embodiment, liquid includes one or more of the following: Calpain I, insulin, adenosine, antioxidants, glutathione peroxidase, vitamin E (alpha tocopherol), $Na^+$—$H^+$ exchange inhibitors, caroporide (HOE 642), agents that open $K_{ATP}$ channels, nitric oxide (NO), endothelin receptor antagonists, tetrahydrobiopterin, statins, sevoflurane, propofol, pinacidil, morphine, verapamil, and blends or mixtures thereof.

Figure 14:
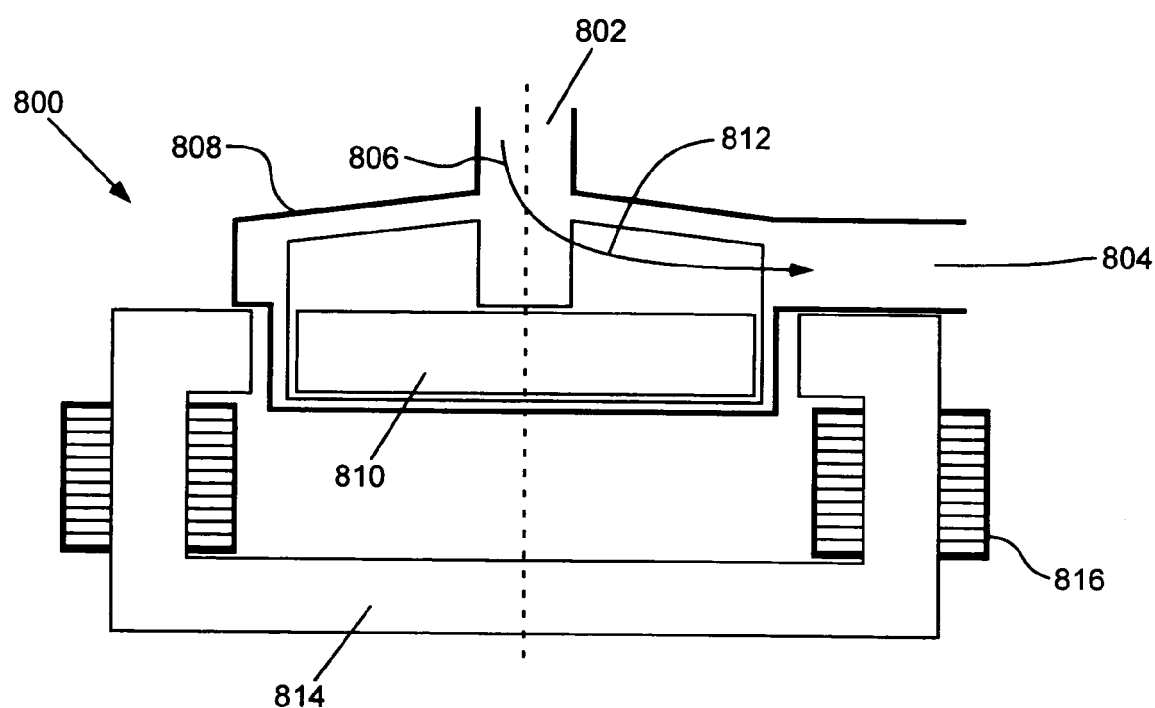
FIG. 14 illustrates a cross-sectional view of a centrifugal pump.

In one embodiment, a pressure increasing device may be attached to fitting 332 at proximal end 326 of catheter 320 to deliver a liquid through delivery lumen 328 (shown in FIGS. 7–9). In one embodiment, the pressure increasing device is a syringe. In another embodiment, the pressure increasing device is a pump, for example, a centrifugal pump, a reciprocating pump, or a gear pump. In one embodiment, the pump is able to achieve a low flow rate at a high pressure. One suitable pump is illustrated in FIG. 14. Centrifugal pump 800 includes inlet 802 and outlet 804 so that the fluid flows as marked by arrow 806. Pump 800 has pump housing 808 to contain fluid and rotor 810 which has impeller 812 attached. In one embodiment, impeller 812 rotates to create a centrifugal force to force fluid from inlet 802 to outlet 804 as shown by arrow 812. Pump 800 also includes stator 814 which has winding 816 attached. In one embodiment, rotor 810 is removably coupled to stator 814, and there is no direct mechanical connection between stator 814 and rotor 810. In one embodiment, rotor 810 and impeller 812 are driven by a magnetic force generated by winding 816. In one embodiment, rotor 810 and pump housing 808 are disposable, while stator 814 and winding 816 are not disposable. In another embodiment, the fluid flows through inlet 802 to outlet 804, which fluid path is sterilized, while stator 814 and winding 816 are not sterilized. One suitable pump can be a disposable infusion pump, for example, manufactured by Pro-Med GmbH. In another embodiment, a suitable pump is a magnetically-levitated centrifugal pump with a disposable rotor chamber, for example, manufactured by Levitronix, Inc.

Figure 16:
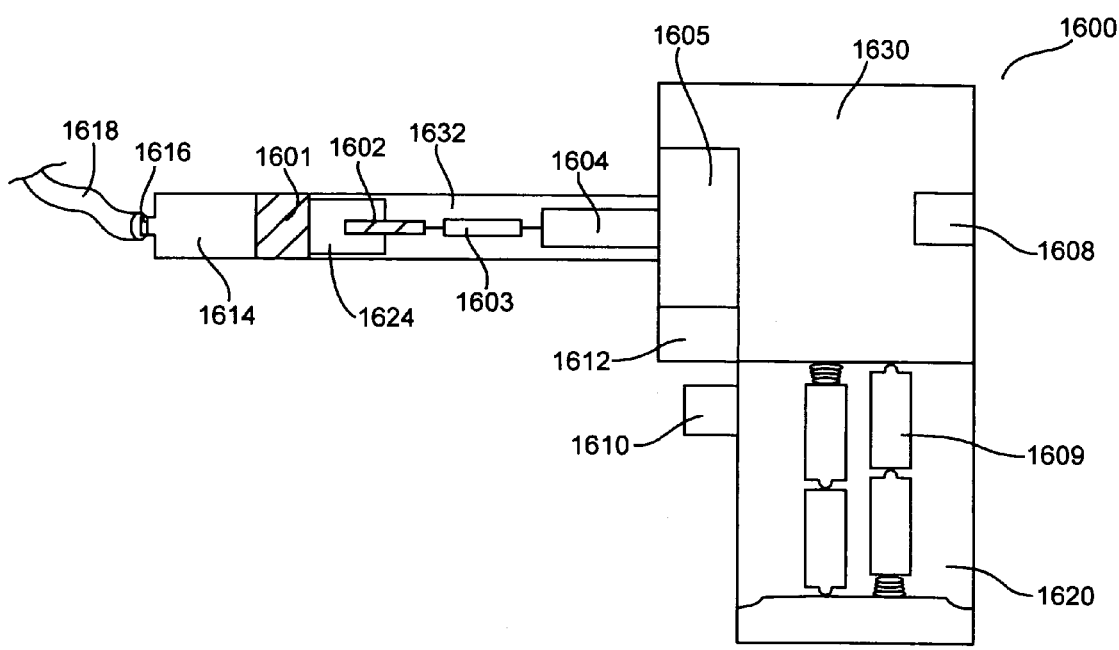
FIG. 16 schematically illustrates a pressure increasing device.

In another embodiment, a suitable pressure increasing device is illustrated in FIG. 16. Pump 1600 includes handle 1620 with batteries 1609, and activator button 1610. Connected to handle 1620 is body 1630 of pump 1600. Body 1630 includes pressure measurement connection 1608, micro-controller 1605, and motor driver chip 1612. Pump 1600 also includes attachment 1632 with motor 1604, motor coupler 1603, where coupler 1603 is connected to lead screw 1602. Lead screw 1602 is fed into non-rotating threaded coupling 1624, so that when motor 1604 is activated, rotational force and motion from motor 1604 is transferred through coupler 1603 to lead screw 1602 to advance or retract non-rotating threaded coupling 1624, depending on the direction of rotation. Non-rotating threaded coupling 1624 is attached to plunger 1601, so that when non-rotating threaded coupling 1624 moves, plunger 1601 also moves. Plunger 1601 can move distally to make reservoir 1614 smaller, or proximally to make reservoir 1614 larger. At the distal end of reservoir 1614 is nozzle 1616 attached to outlet 1618.

In operation, user (not shown) may activate pump 1600 by pressing button 1610. Pressing button 1610 causes micro-controller 1605 to activate, which in turn activates motor driver chip 1612 which sends a current from batteries 1609 to motor 1604. This causes motor 1604 to rotate, sending a rotational motion and force through coupler 1603 to lead screw 1602. Rotating lead screw 1602 causes non-rotating threaded coupling and plunger 1601 to advance or retract, depending on the rotation of motor 1604 and lead screw 1602. Advancing plunger 1601 causes an increase in pressure and a decrease in volume in reservoir 1614 causing fluid or gas stored in reservoir 1614 to be forced through nozzle 1616 and into outlet 1618. In one embodiment, in order to maintain a suitable pressure, pressure feedback from the patient may be received into pump 1600 through pressure measurement connection 1608, which pressure information is fed to micro-controller 1605, which activates motor driver chip 1612, to activate motor 1604 to increase pressure, or to deactivate motor 1604 to allow pressure to drop, or to reverse the direction of motor 1604 to decrease pressure.

Figure 17:
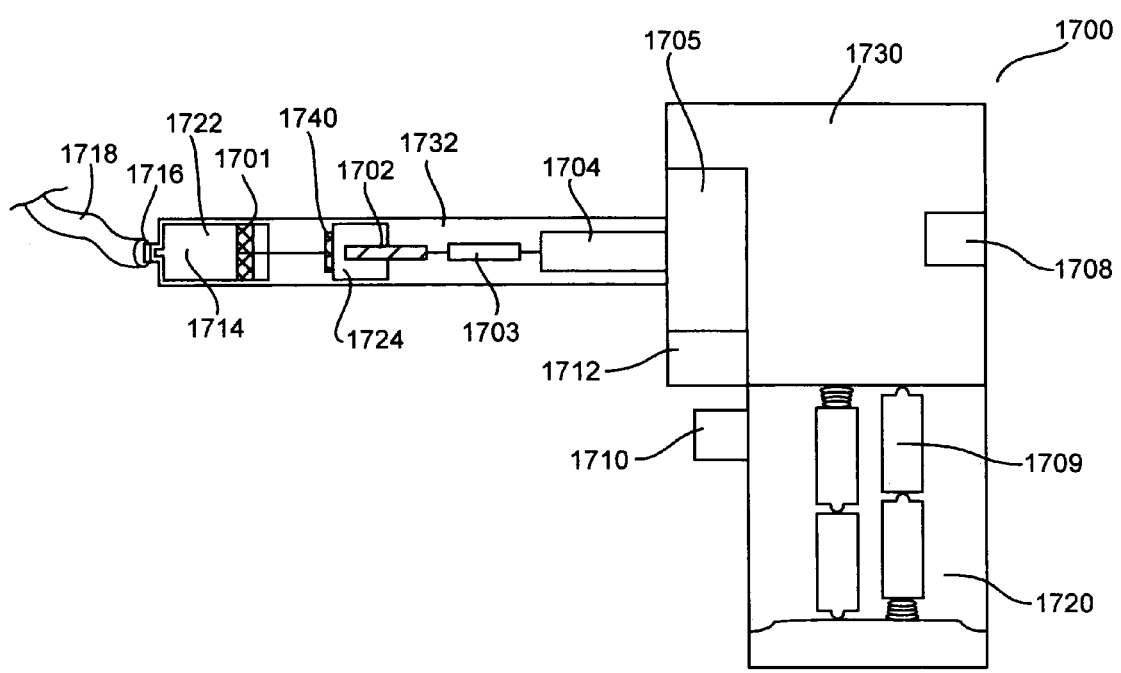
FIG. 17 schematically illustrates a pressure increasing device.

Another suitable pressure increasing device is illustrated in FIG. 17. Pump 1700 includes handle 1720 having batteries 1709, and activation button 1710. Handle 1720 is connected to body 1730, which includes pressure measurement connection 1708, motor driver chip 1712, and micro-controller 1705. Connected to body 1730 is attachment 1732 with motor 1704, coupler 1703, and lead screw 1702. Lead screw 1702 feeds into non-rotating threaded coupling 1724, which is attached to syringe and/or abutted against head 1740. Syringe 1722 is located in a suitably shaped opening, the distal end of handle 1732, and includes syringe head 1740, plunger 1701, reservoir 1714, and nozzle 1716. Nozzle 1716 feeds into outlet 1718. In another embodiment, syringe 1722 may be disposable and thrown away after each treatment. In another embodiment, syringe 1722 may be removed and cleaned and/or sterilized prior to the next treatment.

In another embodiment, pump 1700 may have multiple syringes with different treatment agents.

In operation, pump 1700 may be activated by a user (not shown) by button 1710, which activates micro-controller 1705, which activates motor driver chip 1712, which in turn activates motor 1704, by sending a current from batteries 1709 to motor 1704. Motor 1704 rotates coupler 1703, which rotates lead screw 1702 to advance or retract non-rotating threaded coupling 1724, which serves to advance or retract syringe head 1740, respectively. If syringe head 1740 is advanced, plunger 1701 is also advanced towards the distal end of handle 1732 which serves to increase the pressure and decrease the volume of reservoir 1714, which forces fluid or gas stored in reservoir 1714 through nozzle 1716 and into outlet 1718. If syringe head 1740 is pulled towards proximal end of handle 1732, then the pressure in reservoir 1714 is lowered, and the volume in reservoir 1714 is increased, and fluid may be pulled from outlet 1718 through nozzle 1716 and into reservoir 1714. In one embodiment, a pressure measurement from the patient may be delivered into pump 1700 through pressure measurement connection 1708, which information is fed to micro-controller 1705 then into motor driver chip 1712 which is used to control motor 1704 to advance or retract syringe head 1740 to raise or lower pressure in reservoir 1714, respectively.

Figure 18:
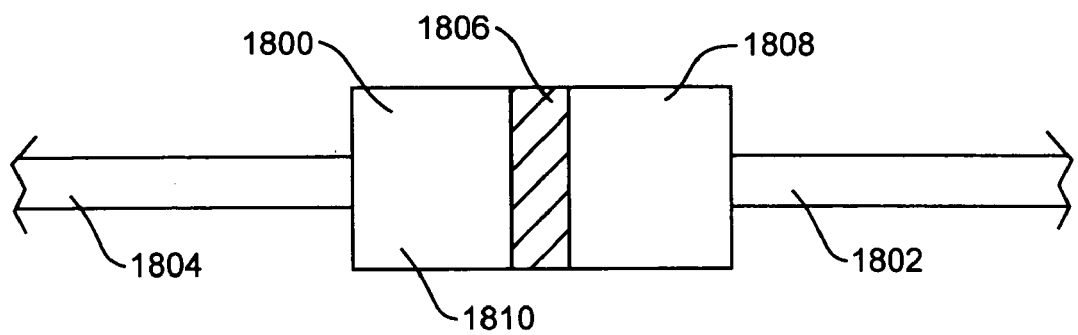
FIG. 18 schematically illustrates a pressure transferring device.

Referring now to FIG. 18, there is illustrated a suitable pressure transferring device. Pressure transferring device 1800 includes fluid inlet 1802, and fluid outlet 1804. Plunger 1806 is located in device 1800, which plunger 1806 serves to separate inlet reservoir 1808 from outlet reservoir 1810. As a fluid is pumped into inlet 1802, fluid enters inlet reservoir 1808 and exerts a force upon plunger 1806. This forces plunger 1806 distally, which increases the pressure and lowers the volume of outlet reservoir 1810, which forces the fluid in outlet reservoir 1810 into outlet 1804. Conversely, when a fluid is forced into outlet 1804 and into outlet reservoir 1810, it exerts a force on plunger 1806, and forces plunger 1806 proximally, which increases the pressure and lowers the volume of inlet reservoir 1808 and forces the fluid in inlet reservoir 1808 into inlet 1802. Device 1800 serves to equalize the pressures in inlet 1802 and inlet reservoir 1808, with the pressures in outlet 1804 and outlet reservoir 1810. Device 1800 may be used immediately before a catheter, so that a relatively expensive treatment agent can be placed in outlet reservoir 1810 and outlet 1804, while a relatively inexpensive liquid, for example a saline solution or water, can be placed in inlet reservoir 1808 and inlet 1802, with a pump (not shown) or other pressure increasing device connected to inlet 1802.

Figure 19:
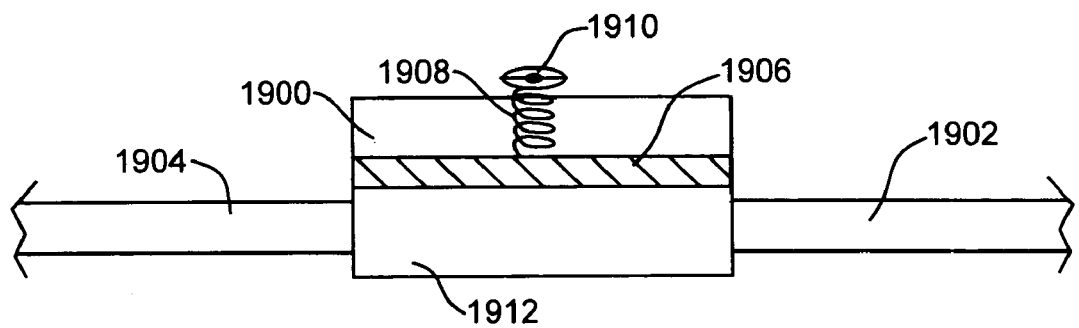
FIG. 19 schematically illustrates a pressure-maintaining or dampening device.

Referring now to FIG. 19, is a pressure-maintaining or dampening device 1900. Device 1900 has inlet 1902 and outlet 1904. Inside device 1900 is plunger 1906 which serves to seal fluid into pressure reservoir 1912. As fluid flows from inlet 1902 into pressure reservoir 1912, the fluid exerts a force on plunger 1906 which compresses spring 1908, until the force exerted by spring 1908 equals the force exerted by the fluid in pressure reservoir 1912 on plunger 1906. When the fluid stops flowing from inlet 1902 into pressure reservoir 1912, there will be a fluid flow provided to outlet 1904 as plunger 1906 is forced down by compressed spring 1908, decreasing the size of fluid reservoir 1912. This downward movement of plunger 1906 continues until pressure in pressure reservoir 1912 equals downward pressure exerted by spring 1908. In another embodiment, spring adjusting device 1910 may be provided to adjust the tension of spring 1908, so that more or less force is required to compress spring 1908.

Figure 20:
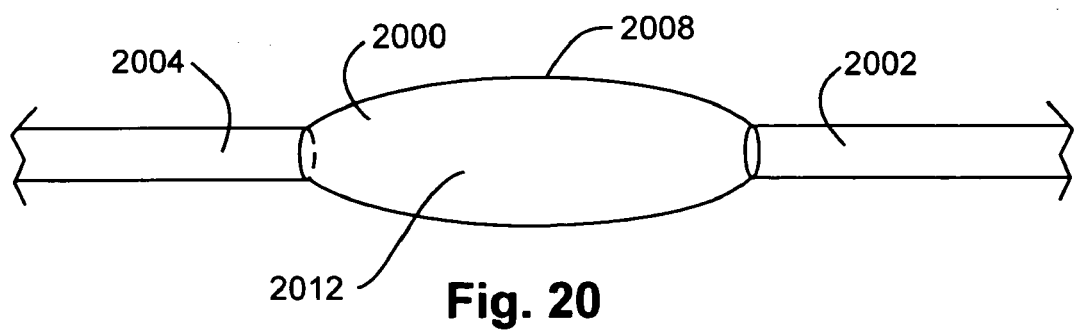
FIG. 20 schematically illustrates a pressure-maintaining or dampening device with inlet and outlet.

Referring now to FIG. 20, is a pressure-maintaining or dampening device 2000, with inlet 2002 and outlet 2004. As fluid flows through inlet 2002 and into pressure reservoir 2012, the fluid causes reservoir 2012 to force walls 2008 of device 2000 outwards until the inward force exerted by walls 2008 equals the outward force exerted by fluid in pressure reservoir 2012. When the fluid flow through inlet 2002 stops, fluid flow to outlet 2004 continues until force exerted by walls 2008 equals force exerted by fluid in pressure reservoir 2012. Walls 2008 may be made of a flexible material, for example rubber. Materials and thickness of walls 2008 may be adjusted so that an appropriate pressure may be maintained within fluid reservoir 2012.

Figure 21:
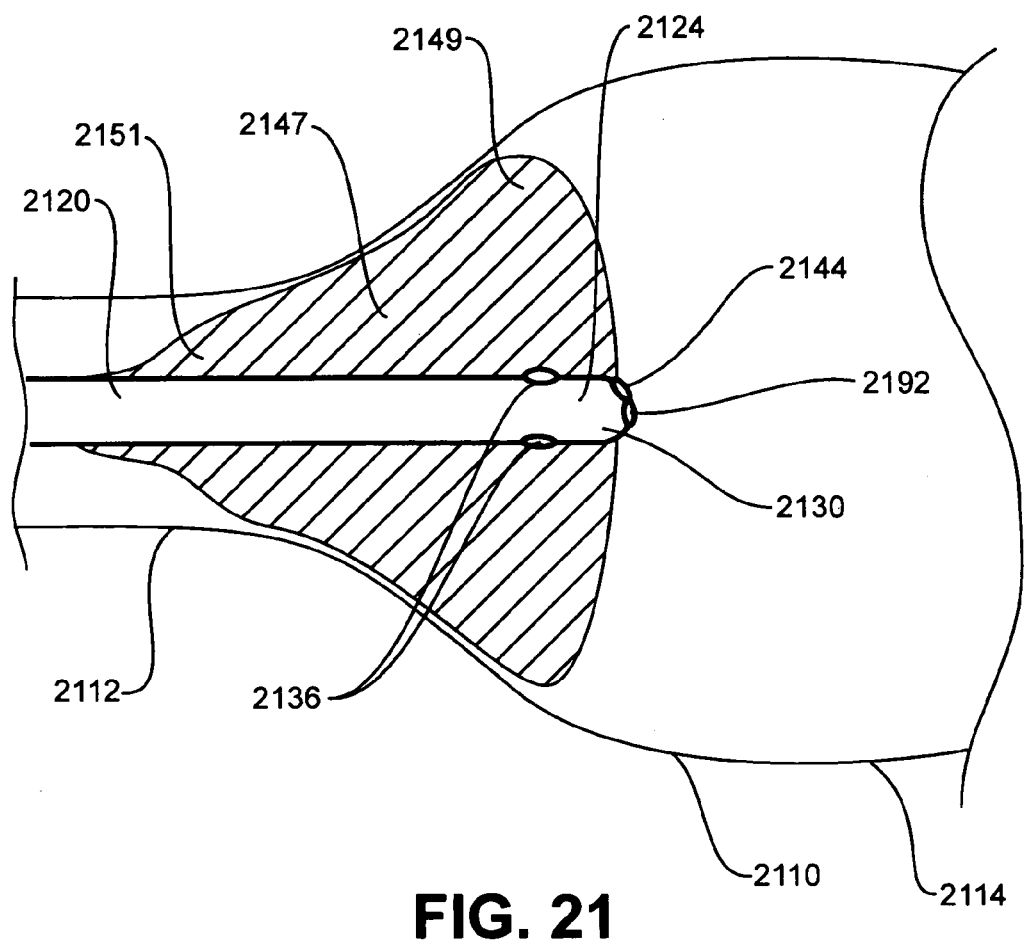
FIG. 21 schematically illustrates a catheter within a vein.

Referring now to FIG. 21, which shows catheter 2120 within vein 2110. Catheter 2120 includes balloon 2147 on distal end 2124 of catheter 2120. Also, on distal end 2124 is outlet port 2192 to deliver a treatment agent into vein 2110. Pressure port 2144 is on distal end 2124 to measure a pressure in vein 2110. Balloon 2147 is inflated by outlet ports of inflation lumen 2136. Vein 2110 is divided into two portions, first portion 2114 is distal to balloon 2147, and second portion 2112 is proximal to balloon 2147. Balloon 2147 serves to seal against inner wall of vein 2110, and provide a pressure separation between first portion 2114 and second portion 2112. In one embodiment, treatment agent flowing through outlet port 2192 serves to increase the size of first portion 2114 due to the high pressure exerted by treatment agent on vein walls in first portion 2114. This causes first portion 2114 to have a larger diameter than second portion 2112, and a frusto-conical shape taper is created between first portion 2114 and second portion 2112. In this embodiment, balloon 2147 is tapered to accommodate the frusto-conical shape of the taper between first portion 2114 and second portion 2112.

In one embodiment, balloon 2147 may be tapered by having distal end 2149 of balloon have a thinner wall thickness than proximal end 2151 of balloon 2147, so that fluid or gas inserted into balloon 2147 through outlet port of inflation lumen 2136 serves to make the distal end 2149 of balloon larger than proximal end 2151 of balloon 2147. In another embodiment, balloon 2147 may have uniform wall thickness of proximal end 2151 and distal end 2149, but the balloon is molded and/or formed in a tapered shape, or otherwise formed so that balloon 2147 will assume a tapered shape when inflated.

In one embodiment, a pressure-sensing device is attached to fitting 348 at proximal end of extension tube 346 of catheter 320 (shown in FIGS. 7–9). In one embodiment, pressure-sensing device may be attached to proximal end of pressure lumen 342 (shown in FIG. 9). In another embodiment, a pressure-sensing device may be fed through pressure lumen 342 adjacent to pressure port 344 on side wall of shaft 322 near distal end 324 of catheter 320 (shown in FIGS. 7–9). In one embodiment, pressure-sensing device is disposable. In another embodiment, pressure-sensing device is a disposable piezo-electric pressure sensor, for example, a piezo-electric pressure sensor manufactured by Utah Medical Products, Inc., which is attached to fitting 348 (shown in FIG. 7).

In one embodiment, an inflation device is attached to fitting 340 at proximal end of inflation extension tube 338 attached to shaft 322 and inflation lumen 336 extending through catheter 320. In one embodiment, the inflation device is a syringe. In another embodiment, the inflation device is a pump, for example, a centrifugal pump, a gear pump, or a reciprocating pump. In another embodiment, balloon 347 is inflated with carbon dioxide, saline, and/or contrast medium by the inflation device.

Figure 15:
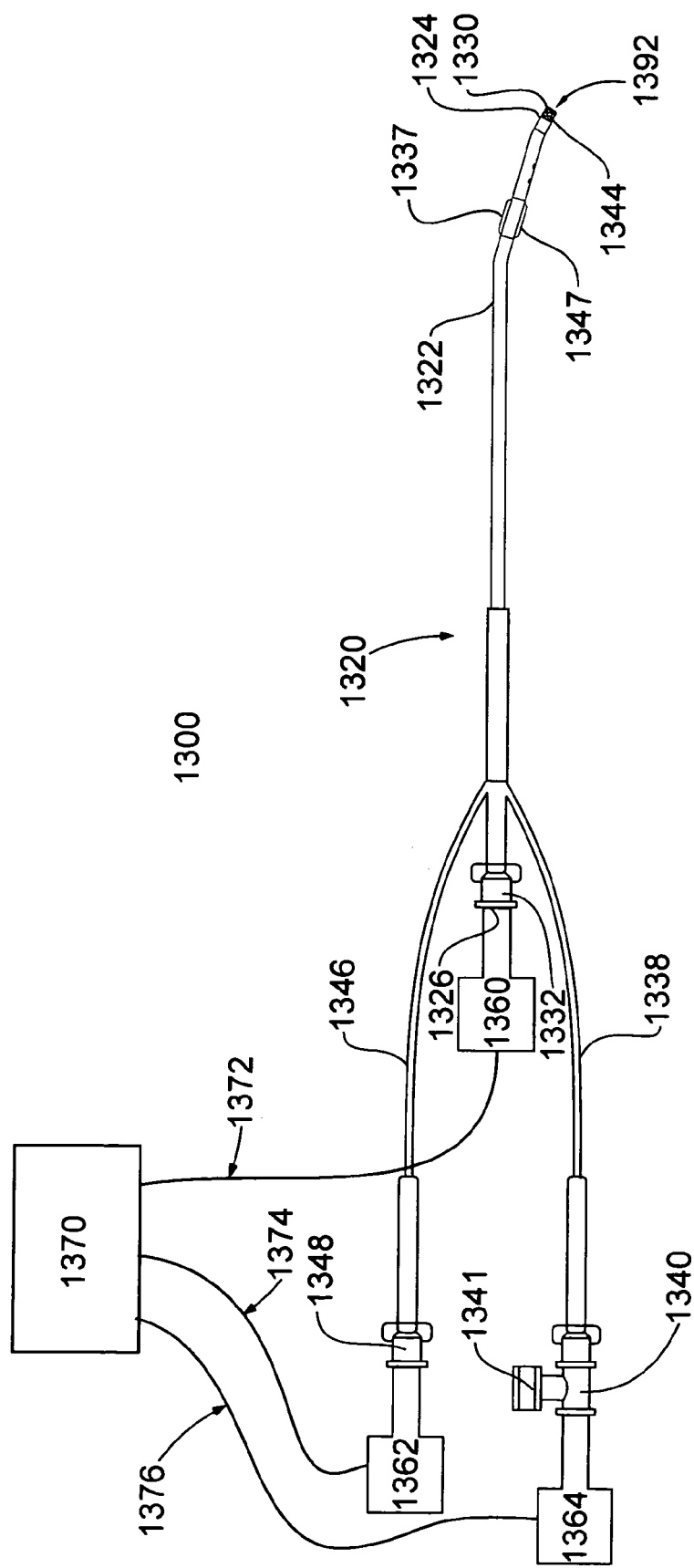
FIG. 15 schematically illustrates a delivery catheter system.

FIG. 15 illustrates a catheter system. Catheter system 1300 includes delivery catheter 1320 having flexible shaft 1322, distal end 1324, proximal end 1326, with a delivery lumen extending therebetween. Soft tip 1330 is bonded to distal end 1324 of shaft 1322. The delivery lumen extends from fitting 1332 at proximal end 1326 through shaft 1322 and through soft tip 1330 to outlet port 1392 in soft tip 1330. One or more side holes in communication with the delivery lumen may also be provided near distal end 1324 of shaft 1322. Pressure increasing device 1360 is shown attached to fitting 1332.

Catheter 1320 is provided with balloon 1347 on distal end 1324 of catheter 1320, which balloon 1347 is adapted to occlude the coronary sinus or another vessel when inflated. An inflation lumen extends through shaft 1322 and is in communication with the interior of balloon 1347 through opening 1337. Near proximal end 1326, the inflation lumen is connected to inflation extension tube 1338 attached to shaft 1322 having fitting 1340 at its proximal end shown attached to inflation device 1364. Optionally, pressure release valve 1341 may be connected to inflation extension tube 1338 to prevent over inflation of balloon 1347.

A pressure lumen is also provided in shaft 1322 which opens at pressure port 1344 on side wall of shaft 1322 near distal end 1324, or in soft tip 1330 as illustrated. The pressure lumen is connected to extension tube 1346 attached to shaft 1322 near proximal end 1326. Extension tube 1346 has fitting 1348 at its proximal end shown connected to pressure measuring device 1362.

Pressure increasing device 1360 is shown connected by connection 1372 to controller 1370. Pressure measuring device 1362 is shown connected to controller 1370 by connection 1374. Inflation device 1364 is shown connected to controller 1370 by connection 1376.

In one embodiment, distal end 1324 of catheter 1320 is inserted into a vessel, for example, the coronary sinus. Once distal end 1324 of catheter 1320 is in place, balloon 1347 may be inflated by inflation device 1364. Pressure measuring device 1362 measures pressure distal to balloon 1324 through pressure port 1344 on side wall of shaft 1322. Once the pressure waveform in the vessel has become ventricularized, for example, blood beating against balloon 1347 in a similar rhythm to a heartbeat, inflation of balloon 1347 is stopped by controller 1370. At this point, pressure increasing device 1360 begins to force a liquid through catheter 1320 to soft tip 1330 to outlet port 1392. Liquid is forced into the vessel distal to balloon 1347. Pressure measuring device 1362 measures pressure distal of balloon while liquid is being forced by pressure increasing device 1360. Controller 1370 controls pressure increasing device 1360 to regulate fluid flow and pressure, by the information provided by pressure measuring device 1362. After a sufficient period of time, controller 1370 stops the delivery of liquid by pressure increasing device 1360, then deflates balloon 1347 with inflation device 1364, and catheter 1320 may then be removed from the vessel.

Figure 22:
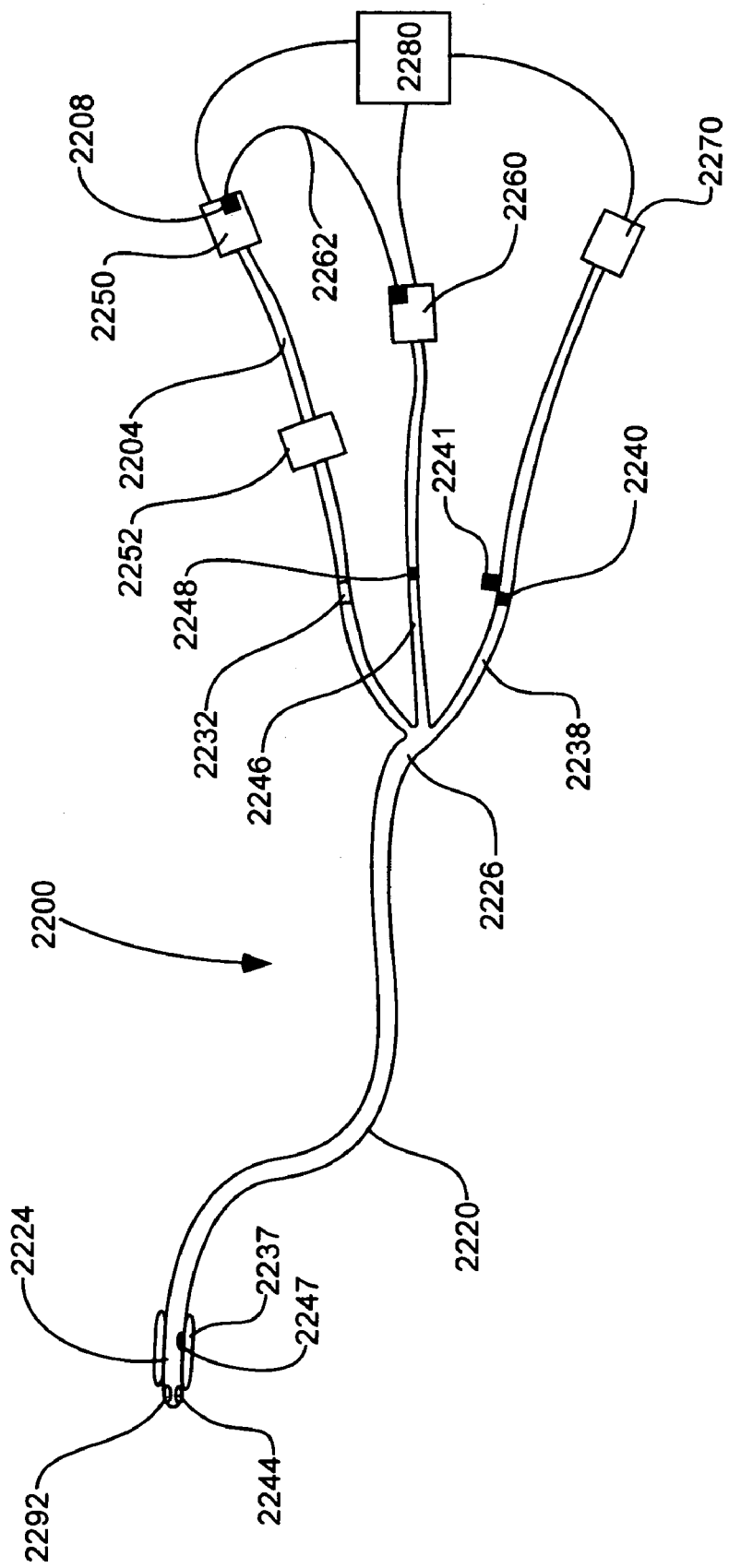
FIG. 22 schematically illustrates a catheter system.

Referring now to FIG. 22, another embodiment of a catheter system is illustrated. Catheter system 2200 includes delivery catheter 2220 (for example, delivery catheter 320, 422, 501, 610, or 2120). Delivery catheter 2220 includes proximal ends 2226 (for example, 326) and distal end 2224 (for example, 324, 512, 660). Delivery catheter 2220 includes a delivery lumen (not shown) (for example, 328). Delivery lumen connects outlet port 2292 (for example, 392, 462, 454, 628, or 2192) on distal end 2224 of catheter with fitting 2232 (for example, 332) on proximal end 2226 of catheter. Fitting 2232 may be connected to a pressure increasing device (for example, 800, 1600, or 1700) by device outlet 2204 (for example, 804, 1618, or 1718). Intermediate to device outlet 2204 and fitting 2232 there may be located one or more (in series) of pressure-transferring device, pressure-maintaining, and/or pressure-dampening device 2252 (for example, 1800, 1900, 2000).

On distal end 2224 of catheter is located balloon 2247 with inflation lumen (not shown) (for example, 336 or 2136), where inflation lumen has opening 2237 (for example, 337, 472), which serves to inflate and/or deflate balloon 2247. Inflation lumen is through catheter 2220 from opening 2237 (for example, 337 or 472) to inflation extension tube 2238 (for example, 338), which has fitting 2240 (for example, 340) at the proximal end of inflation extension tube 2238. There is also optionally provided pressure relief valve 2241 (for example, 341) adjacent to fitting 2240. Inflation device 2270 may be connected to fitting 2240.

Delivery catheter 2220 may also have a pressure lumen (not shown) (for example, 342, 442, or 620), where pressure lumen has pressure port 2244 (for example, 344, 436, 628, 2144) at distal end of pressure lumen. Pressure lumen extends from pressure port 2244 to extension tube 2246 (for example, 346). Extension tube 2246 has fitting 2248 (for example, 348) at proximal end of extension tube 2246. Pressure sensing device 2260 may be connected to fitting 2248.

In one embodiment, pressure sensing device 2260 may be connected to pressure measurement connection 2208 (for example, 1608 or 1708) of pressure increasing device 2250 by pressure measurement connection 2262.

Optionally, there may be provided system controller 2280, for example, a computer or mini-computer, which is connected to pressure increasing device 2250, pressure sensing device 2260, and/or inflation device 2270.

FIG. 23 illustrates a balloon outside diameter growth rate. The balloon has a growth rate or elasticity of about 25% at a pressure of about 2 atmospheres. In another embodiment, the balloon has a growth rate or elasticity of about 40% at a pressure of about 3.5 atmospheres.

Figure 24:
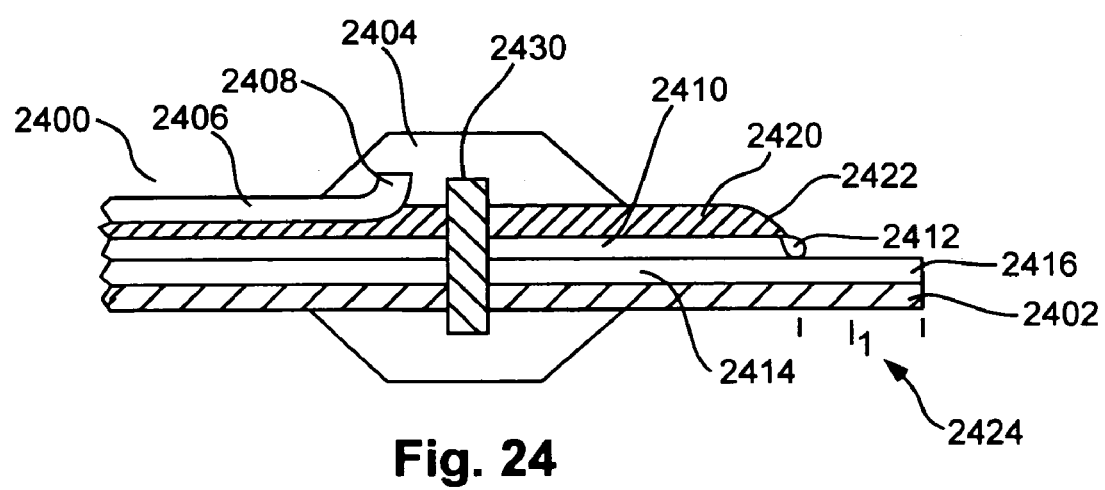
FIG. 24 illustrates a tapered balloon catheter tip.

Referring now to FIG. 24 is a staggered tip of a balloon catheter. Balloon catheter 2400 has distal end 2402 and proximal end (not shown). Adjacent distal end 2402 of catheter is balloon 2404. Balloon inflation lumen 2406 has distal end and opening 2408 within balloon 2404 to inflate and/or deflate balloon 2404. Pressure sensing lumen 2410 has distal end and opening 2412 which enables pressure sensing lumen 2410 to sense pressure or other measurements or parameters wherever distal end 2402 of catheter is placed. Delivery lumen 2414 has distal end and opening 2416 which enables a fluid path from proximal end (not shown) of catheter to distal end 2402 of catheter.

Staggered tip of catheter 2400 may enable easier tracking of distal end 2402 of catheter through a blood vessel. In one embodiment, pressure sensing lumen 2410 and/or catheter body 2420 adjacent pressure sensing lumen 2410 have tapered cut 2422 which may be curved. In one embodiment, distance l1 marked with reference numeral 2424 is the distance between distal end 2412 of pressure sensing lumen 2410 and distal end 2416 of delivery lumen 2414. In one embodiment, l1 2424 may be between about 0.5 millimeters and 5 millimeters.

In another embodiment, catheter 2400 is illustrated. Catheter has balloon inflation lumen 2406, balloon 2404, delivery lumen 2410 having opening 2412, and pressure sensing lumen 2414 having opening 2416. Catheter 2400 has a staggered tip where opening 2412 of delivery lumen 2410 is distance l1 2424 from opening 2416 of pressure sensing lumen 2414. In addition, catheter body 2420 adjacent opening 2412 of delivery lumen 2410 may have a tapered and/or curved shape 2422.

In another embodiment, catheter 2400 may include marker 2430, for example a radio-opaque marker, which may serve to ease visualization of distal end 2402 of catheter 2400 with a diagnostic or visualization system.

Figure 25:
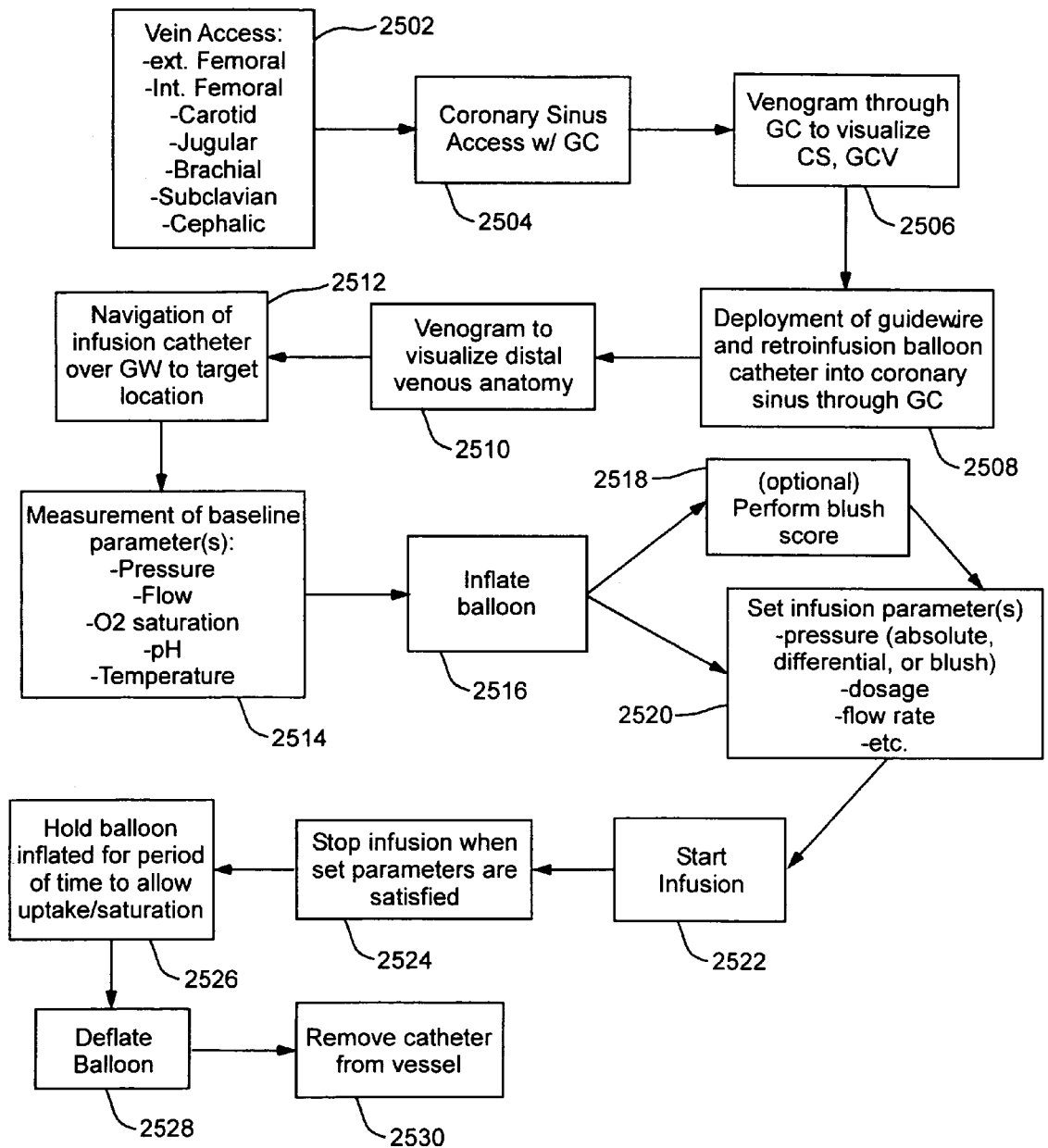
FIG. 25 illustrates a method of treating a patient.

Referring now to FIG. 25, a method of treating a patient is illustrated. First, a vein is accessed 2502 by a catheter, for example, the exterior femoral vein, the interior femoral vein, carotid, jugular, brachial, subclavian, or saphalic vein is accessed by distal end of a guide catheter. Coronary sinus 2504 is accessed with a guide catheter through either the inferior vena cava or superior vena cava. Venogram 2506 is performed through the guide catheter to visualize coronary sinus and/or great cardiac vein. Deployment of guidewire and retroinfusion balloon catheter 2508 into the coronary sinus through the guide catheter 2510. Venogram 2510 to visualize distal venus anatomy. Navigation of infusion catheter over guidewire 2512 to a target location. Measurement of baseline parameters 2514, for example, pressure, flow, oxygen saturation, pH, and/or temperature at the target location. Inflate balloon 2516 to occlude coronary sinus and/or other vessel where balloon catheter has been placed, for example the target location. Perform blush score 2518, an optional step to determine blush pressure. Set infusion parameters 2520, for example, absolute pressure, differential pressure, blush pressure, dosage, and/or flow rate. Start infusion 2522. Optional measuring of infusion parameters and feedback to a controller (not shown). Stop infusion 2524 when set parameters are satisfied. Hold balloon inflated 2526 for a period of time to allow uptake and/or saturation. Deflate balloon 2528. Remove catheter, guide catheter and/or guidewire, from vessel 2530.

In another embodiment, a catheter may be used to locally administer a treatment or therapeutic agent. Copending U.S. Application having Ser. No. 10/246,249 filed on Sep. 18, 2002 discloses suitable treatment agents and suitable methods of administering the treatment agents. Copending U.S. Application having Ser. No. 10/246,249 filed on Sep. 18, 2002 is herein incorporated by reference in its entirety. U.S. Pat. No. 6,346,098, issued to Yock et al., discloses a suitable method of locally administering a treatment agent. U.S. Pat. No. 6,346,098, issued to Yock et al., is herein incorporated by reference in its entirety.

In one embodiment, delivery catheter includes flexible shaft having proximal end and distal end, distal end has an outer diameter less than about 10 mm; delivery lumen having proximal end and distal end, delivery lumen within flexible shaft, delivery lumen having at least one outlet port or at least one side hole at distal end of delivery lumen, delivery lumen has cross-sectional area of at least about 0.95 mm$^2$; pressure monitoring lumen having proximal end and distal end, pressure monitoring lumen within flexible shaft; pressure port adjacent to and connected to distal end of pressure monitoring lumen; balloon inflation lumen having proximal end and distal end, balloon inflation lumen within flexible shaft; soft tip at distal end of flexible shaft; balloon at distal end of flexible shaft, balloon adjacent to and connected to distal end of balloon inflation lumen, balloon having at least one material selected from polyether block amide resin, polyurethane, silicone, natural latex, or synthetic latex; wherein balloon is adapted to inflate to a diameter range of about 4 to about 9 mm.

In another embodiment, distal end has an outer diameter less than about 7 mm. In another embodiment, distal end has an outer diameter less than about 5 mm. In another embodiment, distal end has an outer diameter less than about 3 mm.

In another embodiment, delivery lumen has cross-sectional area of at least about 3 mm$^2$. In another embodiment, delivery lumen has cross-sectional area of at least about 5 mm$^2$. In another embodiment, delivery lumen has cross-sectional area of at least about 10 mm$^2$.

In another embodiment, flexible shaft is made of a bio-compatible polymer. In another embodiment, flexible shaft is made of a bio-compatible polymer having a durometer hardness of about 30 to about 100 shore D. In another embodiment, flexible shaft is made of a bio-compatible polymer having a durometer hardness of about 50 to about 70 shore D. In another embodiment, flexible shaft is made of polyether block amide resin. In another embodiment, flexible shaft is radiopaque.

In another embodiment, delivery catheter includes pressure relief valve adjacent to proximal end of balloon inflation lumen.

In another embodiment, delivery catheter includes liquid, liquid having at least one of a treatment agent and a drug. In another embodiment, liquid includes at least one material selected from antibodies against CD 11/18, P-selectin, L-selectin, ICAM, VCAM, IGF-I, estrogen, GIK solution, adenosine, isoforms of adenosine, Na/H exchangers, Na/K exchangers, cardiomyocites, multi-potent cells, ologo-potent cells, stem cells, progenitor cells, angiogenic cells, structural cells, skeletal cells, smooth muscle cells, BEGF, FGF, HGF, calpain I, insulin, antioxidants, glutathione peroxidase, vitamin E, Na+—H+ exchange inhibitors, caroporide, nitric oxide, endothelin receptor antagonists, tetrahydrobiopterin, statins, sevoflurane, propofol, pinacidil, morphine, or verapamil.

In another embodiment, balloon includes a coating, for example on balloon's outside surface. In another embodiment, balloon has a conical shape. In another embodiment, balloon is made of a material adapted to improve control of expansion diameter.

In another embodiment, delivery catheter has pressure increasing device connected to proximal end of delivery lumen, pressure increasing device selected from syringes, reciprocating pumps, gear pumps, or centrifugal pumps. In another embodiment, pressure increasing device is a centrifugal pump having a removable and disposable rotor and pump housing.

In another embodiment, delivery catheter has pressure sensing device connected to proximal end of pressure monitoring lumen. In another embodiment, pressure sensing device is a disposable piezo-electric pressure sensor.

In another embodiment, delivery catheter has inflation device connected to proximal end of balloon inflation lumen, inflation device selected from syringes, reciprocating pumps, gear pumps, or centrifugal pumps.

In another embodiment, delivery catheter has inflation extension tube adjacent to and connected to proximal end of inflation lumen.

In another embodiment, delivery catheter has pressure monitoring extension tube adjacent to and connected to proximal end of pressure monitoring lumen.

In one embodiment, catheter kit has delivery catheter that includes flexible shaft having proximal end and distal end, distal end has an outer diameter less than about 10 mm, delivery lumen having proximal end and distal end, delivery lumen within flexible shaft, delivery lumen having at least one outlet port or at least one side hole at distal end of delivery lumen, delivery lumen has cross-sectional area of at least about 2 mm$^2$, pressure monitoring lumen having proximal end and distal end, pressure monitoring lumen within flexible shaft, pressure port adjacent to and connected to distal end of pressure monitoring lumen, balloon inflation lumen having proximal end and distal end, balloon inflation lumen within flexible shaft; soft tip at distal end of flexible shaft, balloon at distal end of flexible shaft, balloon adjacent to and connected to distal end of balloon inflation lumen, balloon having at least one material selected from polyether block amide resin, polyurethane, silicone, natural latex, or synthetic latex, wherein balloon is adapted to inflate to a diameter range of about 4 to about 9 mm; guide catheter adapted to receive delivery catheter; pressure increasing device adapted to connect to proximal end of delivery lumen; pressure sensing device adapted to connect to proximal end of pressure monitoring lumen; inflation device adapted to connect to proximal end of balloon inflation lumen; and guidewire adapted to be received within guide catheter.

In another embodiment, catheter kit has controller adapted to control pressure increasing device, pressure sensing device, and inflation device.

In one embodiment, method of providing treatment in vessel of patient that includes placing delivery catheter in vessel of patient; measuring pressure in vessel adjacent to distal end of catheter; inflating balloon at distal end of catheter; stopping inflation of balloon when measured pressure waveform becomes ventricularized; forcing liquid having at least one drug and/or one treatment agent through catheter to outlet port on catheter distal to balloon; stopping forcing of liquid; deflating balloon; and removing catheter from vessel.

In another embodiment of method, vessel is coronary sinus of patient.

In another embodiment of method, controller is used to control inflating balloon, stopping inflation of balloon, forcing liquid through catheter, stopping forcing of liquid, and deflating balloon.

Throughout the application, references have been made to a pressure lumen and a pressure sensing device, while the pressure lumen can be used for measuring other parameters including flow, oxygen saturation, pH, and/or temperature, and/or others. Similarly, pressure sensing device can be exchanged with another device to measure one of the other parameters. Similarly, catheters have been illustrated with three lumens, while it is envisioned that these catheters can be replaced with other catheters with four or more lumens, for example, a balloon inflation lumen, a delivery lumen, and two parameter measurement lumens, for example, one lumen to measure pressure, and one to measure temperature, for example.

In the preceding detailed description, reference to specific embodiments were described. It will, however, be evident that various modifications and changes may be made thereto without departing from the broader spirit and scope of the appended claims. The specification and drawings are, accordingly, to be regarded in an illustrative rather than a restrictive sense.

What is claimed is:

1. A method comprising:
    accessing a vein selected from the group consisting of external femoral, interior femoral, carotid, jugular, brachial, subclavian, and cephalic with a guide catheter;
    accessing a coronary sinus with the guide catheter;
    feeding a guidewire and a retroinfusion balloon catheter to the coronary sinus through the guide catheter;
    performing a venogram;
    deploying the guidewire and the balloon catheter to a targeted vein;
    measuring a baseline parameter in the vein adjacent to a distal end of the balloon catheter;
    inflating a balloon at the distal end of the balloon catheter to a pressure sufficient to make a pressure waveform in the vein become ventricularized;

after inflating the balloon, delivering a liquid comprising at least one of a drug and a treatment agent through the balloon catheter to an outlet port on the balloon catheter distal to the balloon;

stopping the delivering of the liquid;

deflating the balloon; and removing the catheter from the vessel.

2. The method of claim 1, further comprising performing an infusate-uptake-enhancing procedure selected from the group consisting of electroporation, ultrasonic excitation, and photodynamic therapy.

3. The method of claim 1, wherein the target vein is selected from the group consisting of coronary sinus, great cardiac vein, anterior interventricular vein, oblique vein of left atrium, posterior vein of left ventricle, middle cardiac vein, small cardiac vein, lateral vein, and anterior cardiac vein of right ventricle.

4. The method of claim 1, wherein the liquid comprises a material selected from the group consisting of cells, and endothelial cells, antibodies against CD18, CD 11/18, P-selectin, L-selectin, ICAM, VCAM, and TNF, estrogen and estrogen receptor agonists, growth factors and their isofoms and downstream signaling mediators, heat shock proteins and their downstream signaling mediators, GIK, adenosine and adenosine receptor agonists, NO donors, Na/H exchange inhibitors, Na/K channel openers and their downstream signaling mediators, Ca channel inhibitors, beta-adrenergic receptor inhibitors, alpha-adrenergic receptor inhibitors, free radical scavengers, anti-oxidants, platelet inhibitors such as IIbIIIa receptor antagonists, complement system inhibitors, anti-apoptotic drugs, genes that encode peptides listed above or their ligands, or bio-engineered cells or materials that express peptides or glycoproteins or their ligands, and mixtures thereof.

5. The method of claim 1, wherein accessing the coronary sinus with the guide catheter further comprises:

feeding the guide catheter into the femoral vein;

feeding the guide catheter into a inferior vena cava;

feeding the guide catheter into a right atrium; and feeding the guide catheter into a coronary sinus.

* * * * *

UNITED STATES PATENT AND TRADEMARK OFFICE
CERTIFICATE OF CORRECTION

| | |
|---|---|
| PATENT NO. | : 7,250,041 B2 |
| APPLICATION NO. | : 10/387048 |
| DATED | : July 31, 2007 |
| INVENTOR(S) | : Jessica Chiu et al. |

Page 1 of 1

It is certified that error appears in the above-identified patent and that said Letters Patent is hereby corrected as shown below:

Title Page, Item (75) Inventors: please delete "Poster" and insert --Foster--.

Signed and Sealed this

Eighteenth Day of May, 2010

David J. Kappos
*Director of the United States Patent and Trademark Office*